(12) United States Patent
Martin et al.

(10) Patent No.: US 7,151,102 B2
(45) Date of Patent: Dec. 19, 2006

(54) PHTHALAZINONE DERIVATIVES

(75) Inventors: Niall Morrison Barr Martin, Cambridge (GB); Graeme Cameron Murray Smith, Cambridge (GB); Charles Richard White, Carlisle (GB); Roger Frank Newton, Cornwall (GB); Diane Gillian Douglas, Cornwall (GB); Penny Jane Eversley, Cornwall (GB); Julia Vile, Cornwall (GB)

(73) Assignees: Kudos Pharmaceuticals Limited, Cambridge (GB); Maybridge PLC, Cornwall (GB)

( * ) Notice: Subject to any disclaimer, the term of this patent is extended or adjusted under 35 U.S.C. 154(b) by 181 days.

(21) Appl. No.: 10/021,506

(22) Filed: Oct. 30, 2001

(65) Prior Publication Data

US 2002/0183325 A1  Dec. 5, 2002

Related U.S. Application Data

(60) Provisional application No. 60/275,066, filed on Mar. 12, 2001, provisional application No. 60/245,662, filed on Nov. 6, 2000.

(30) Foreign Application Priority Data

Oct. 30, 2000  (GB) ................ 0026505.8

(51) Int. Cl.
C07D 237/26 (2006.01)
C07D 487/00 (2006.01)
A01N 43/58 (2006.01)
A61K 31/50 (2006.01)

(52) U.S. Cl. ............... 514/248; 544/233; 544/235; 544/237

(58) Field of Classification Search ............... 514/248, 514/252.01, 252.02, 252.03, 252.04, 252.05, 514/252.06; 544/234, 235, 237, 233
See application file for complete search history.

(56) References Cited

U.S. PATENT DOCUMENTS

| | | | |
|---|---|---|---|
| 3,813,384 A | 5/1974 | Vogelsang et al. | |
| 4,665,181 A | 5/1987 | Thomas et al. | |
| 4,841,047 A | 6/1989 | Engel et al. | |
| 5,032,617 A | 7/1991 | Lee et al. | |
| 5,041,653 A | 8/1991 | Lee et al. | |
| 5,215,738 A | 6/1993 | Lee et al. | |
| 5,556,856 A | 9/1996 | Engel et al. | |
| 5,587,384 A | 12/1996 | Zhang et al. | |
| 5,648,355 A | 7/1997 | Theoharides | |
| 5,874,444 A | 2/1999 | West | |
| 6,197,785 B1 | 3/2001 | Jackson et al. | |
| 6,340,684 B1 * | 1/2002 | Napoletano et al. | ........ 514/248 |
| 6,426,415 B1 | 7/2002 | Jackson et al. | |
| 6,476,048 B1 | 11/2002 | Szabo et al. | |
| 6,498,160 B1 * | 12/2002 | Napoletano et al. | ........ 514/248 |
| 6,514,984 B1 | 2/2003 | Watanabe | |
| 6,635,642 B1 | 10/2003 | Jackson et al. | |
| 2004/0023968 A1 | 2/2004 | Martin et al. | |
| 2005/0080096 A1 | 4/2005 | Ishida et al. | |

FOREIGN PATENT DOCUMENTS

| | | |
|---|---|---|
| DE | 3813531 | 4/1988 |
| EP | 0 355 750 | 2/1990 |
| EP | 0 590 551 | 4/1994 |
| EP | 0 634 404 A1 | 1/1995 |
| EP | 0705903 | 4/1996 |
| EP | 0 792 643 | 9/1997 |
| FR | 2262513 | 9/1975 |
| GB | 2384776 | 3/2004 |
| IT | MI98A001671 | 4/1999 |
| JP | 62-252774 | 11/1987 |
| WO | WO 91/18591 | 12/1991 |
| WO | WO 94/10151 | 5/1994 |
| WO | WO 95/24379 | 9/1995 |
| WO | WO 96/19225 | 6/1996 |
| WO | WO 98/43477 | 10/1998 |
| WO | WO 99/08680 | 2/1999 |
| WO | WO 99/11624 | 3/1999 |
| WO | WO 99/11645 | 3/1999 |

| | | |
|---|---|---|
| WO | WO 99/11649 | 3/1999 |
| WO | WO 99/44612 | 9/1999 |
| WO | WO/00/05219 | 2/2000 |
| WO | WO 00/44726 | 8/2000 |
| WO | WO 00/67734 | 11/2000 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 03/070726 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/063874 | 8/2003 |
| WO | WO 03/070707 | 8/2003 |
| WO | WO 03/080581 | 10/2003 |
| WO | WO 03/093261 | 11/2003 |

OTHER PUBLICATIONS

Fujisawa Pharm., Chemical Abstracts, vol. 109:6531, 1988.*
Islam et al., Chemical Abstracts, vol. 95:187182, 1981.*
Islam et al., Chemical Abstracts, vol. 95:62106, 1981.*
Islam et al., Chemical Abstracts, vol. 87:67943, 1977.*
El-Tamaty, et al, "Sy[n]thesis and biological activity of some 4-benzyl-1(2H)-phthalazinone derivatives," *Chemical Abstracts*, 300924j, v. 125, No. 23 (1996).
El-Tamaty , et al., Synthesis and biological activity of some 4-benzyl-1(2H)-phthalazinone derivatives, *Indian J. Chemistry*, v. 35B, pp. 1067-1072 (Oct. 1996).
Shimizu, T., et al., "Inhibitory effects of Azelastine and Tranilast on leukotriene $C_4$ generation by rat colonic mucosa," *Prostaglandins Leukotrienes and Essential Fatty Acids*, 53, 355-358(1995).
Bold et. al., New Anilinophthalazines as Potent and Orally Well Absorbed Inhibitors of the VEGF Receptor Tyrosine Kinases Useful as Antagonists of Tumor-Driven Angiogenesis, J.Med. Chem, 2000, 43, 2310-2323.
Bold et. al., J. Med. Chem., 2000, 43, 3200.
D'Amours et al., 1999, *Biochem. J.* 342: 249-268.
d'Adda di Fagagna et al., 1999, *Nature Gen.*, 23(1): 76-80.
Althaus, F.R. and Richter, C., 1987, ADP-Ribosylation of Proteins: Enzymology and Biological Significance, Springer-Verlag, Berlin—not being sent.
Rhun et al., 1998, *Biochem. Biophys. Res. Commun.*, 245: 1-10.
Miwa et al., 1977, *Arch. Biochem. Biophys.* 181: 313-321.
Burzio et al., 1975, *Proc. Soc. Exp. Biol. Med.* 149: 933-938.
Hirai et al., 1983, *Cancer Res.* 43: 3441-3446.
Durkacz et al., 1980, *Nature* 283: 593-596.
Berger, N.A., 1985, *Radiation Research*, 101: 4-14.
Ben-Hur et al., 1984, *British Journal of Cancer*, 49 (Suppl. VI): 34-42.
Schlicker et al., 1999, *Int. J. Radiat. Biol.*, 75: 91-100.
Wang et al., 1995, *Genes Dev.*, 9: 509-520.
Ménissier de Murcia et al., 1997, *Proc. Natl. Acad. Sci. USA*, 94: 7303-7307.
Cantoni et al., 1989, *Biochim. Biophys. Acta*, 1014: 1-7.
Szabo, et al., 1997, *J. Clin. Invest.*, 100: 723-735.
Cosi et al., 1994, *J. Neurosci. Res.*, 39: 38-46.
Said et al., 1996, *Proc. Natl. Acad. Sci. U.S.A.*, 93: 4688-4692.
Liaudet et al., 2000, *Proc. Natl. Acad. Sci. U.S.A.*, 97(3): 10203-10208.

Gäken et al., 1996, *J. Virology*, 70(6): 3992-4000.
Rattan and Clark, 1994, *Biochem. Biophys. Res. Comm.*, 201 (2): 665-672.
Berge et al., 1977, "Pharmaceutically Acceptable Salts," *J. Pharm. Sci.*, vol. 66, pp. 1-19. *Protective Groups in Organic Synthesis* (T. Green and P. Wuts, Wiley, 1991).
Yamaguchi, et al., J. Med. Chem. 1993, 36, 4052-4060 *Remington's Pharmaceutical Sciences*, 18th edition, Mack Publishing Company, Easton, Pa., 1990.
Skehan, P., et al., 1990, *J. Natl. Cancer Inst.*, 82, 1107-1112.
Perkins et al., *Cancer Research*, 61, 4175-4183 (2001).
Chemical Abstracts 122:204573, 1995.
Chemical Abstracts 104:102050, 1985.
Chemical Abstracts 134:65983, 2000.
Chemical Abstracts 132:273943, 1999.
Yamaguchi, et al., *J. Med. Chem.*, 36, 4061-4068 & 4052-4060 (1993).
Banasik, et al., *J. Biol. Chem.*, 267, 1569-1575 (1992).
Hall, Wong & Chapman, Anti-Cancer Drugs, vol. 6—1995, pp. 147-155 (relates to a Chem Abs).
Bold, G., et al., *J. Med. Chem.*, 2000, 43, 2310-2323.
UKPO Search Report, 2000.
Martin, N., et al., Abstract 107, ADPR 2001 13th International Symposium on ADP-ribosylation.
Affar, E. B. et al., "Immunodot Blot Method for the Detection of Poly(ADP-ribose) Synthesized in Vitro and in Vivo," *Anal. Biochem.*, 1998, vol. 259, No. 2, 280-3.
Al-Dabbagh and Smith, "Species differences in oxidative drug metabolism: some basic considerations." *Archives of toxicology*, Supplement. *Archiv fur Toxikologie*. Supplement, vol. 7, 219-231 (1984).
Ame et al., *J. Biol. Chem.*, 1999, vol. 274, 17860-17868.
Angell et al., *EMBO J.*, vol. 16, No. 12, 3675-3684.
*Applied Biosystems 430A Users Manual*, ABI Inc., Foster City, California (book not provided).
Arnaudeau, C. et al., *J. Mol. Biol*, 2001, vol. 307, 1235-45.
Banasik, M. et al., *Mol. Cell Biochem.*, 1994, vol. 138, 185-197.
Bodanzsky, M. and Bodanzsky, A., *The Practice of Peptide Synthesis*, 1984, Springer-Verlag, New York (book not provided).
Bowman et al., "Differential effects of the poly (ADP-ribose) polymerase (PARP) inhibitor NU 1025 on topoisomerase I and II inhibitor cytoxicity in L1210 cells in vitro," *British Journal of Cancer*, vol. 84(1), 106-112 (2001).
Bundgaard, H., *Design of Prodrugs*, 1 (1985) Elsevier Science Publishers.
Cosi, C., "New inhibitors of poly(ADP-ribose) polymerase and their potential therapeutic targets," *Expert Opin. Ther. Patents* (2002) 12(7): 1047-1071.
Crooke, *Ann. Rev. Pharmacol. Toxicol.*, 1992, vol. 32, 329-76.
*Current Protocols in Molecular Biology*, 1992, Eds. Ausubel et al., John Wiley & Sons (book not provided).
Dantzer, F. et al., *Biochemistry*, 2000, vol. 39, 7559-69.
Dillon, K. J. et al., *J. Biomolecular Screening*, 2003, vol. 8, No. 3, 347-52.
Ehrlich et al., *Science*, 1991, vol. 252, 1643-50.
*From DNA damage and stress signalling to cell death*, 2000, Eds. De Murcia, G. and Shall, S, Oxford University Press (book not provided).
Green, T. et al., "Protective Groups in Organic Synthesis", 1999, 3 Ed., Wiley (book not provided).
Griffin et al., "The role of inhibitors of poly (ADP-ribose) polymerase as resistance-modifying agents in cancer therapy," *Biochim* vol. 77, 408-422 (1995).
Haber, J. E., *Trends Biochem. Sci.*, 1999, vol. 24, 271-5.
*Handbook of Pharmaceutical Additives*, 2001, 2 Ed., Synapse Information Resources Inc., Endicott, New York, USA (book not provided).
*Handbook of Pharmaceutical Excipients*, 1994, 2 Ed. (book not provided).
*Hawley's Condensed Chemical Dictionary*, 13th ed., Van Nostrand Reinhold eds. 716 and 825 (1997).
Hoeijmakers, J. H., *Nature*, 2001, vol. 411, 366-74.

Kerrigan, F. et al., Poster at 12th SCI-RSC Medicinal Chemistry Symposium, Cambridge, 7-10 (2003).
Lemay, M. et al., *Biotechniques*, 1999, vol. 27, 846-51.
Martin, N. et al., *J. Photochem. and PhotoBiol. B: Biology*, 2001, vol. 63, 162-170.
Mercola, et al., *Cancer Gene Therapy*, 1995, vol. 2, No. 1, 47-59.
*Molecular Cloning: A Laboratory Manual*, 2001, 3 Ed., Sambrook & Russell, Cold Spring Harbor Laboratory Press, New York (book not provided).
Mullis et al., *Cold Spring Harbor Symp. Quant. Biol.*, 1987, vol. 51, 263-273.
Nathanson, K. L. et al., *Nat. Med.*, 2001, vol. 7, 552-6.
Noel, G. et al., *BMC Cell Biol.*, 2003, vol. 4, 7.
Pacher et al., "The Role of Poly(ADP-Ribose) Polymerase Activation in the Development on Myocardial and Endothelial Dysfuntion in Diabetes," Diabetes, 51:514-521 (2002).
*PCR Protocols; A Guide to Methods and Application*, 1990, Eds. Innis et al., Academic Press, New York (book not provided).
*PCR Technology*, 1989, Eds. Ehrlich, Stockholm Press, New York (book not ptovided).
*Remington's Pharmaceutical Sciences*, 2000, 20 Ed., Lippincott, Williams & Wilkins (book not provided).
Schultz, N. et al., *Nucleic Acids Res.*, 2003, vol. 31, 4959-64.
Shall, S. et al., *Mutat. Res.*, 2000, vol. 460, 1-15.
Silverman, R.B., *The Organic Chemistry of Drug Design and Drug Action*, 352-400 (1992) Academic Press, Inc.
Southan, G.J. and Szabo, C., "Poly (ADP-ribose) polymerase inhibitors," *Current Medical Chemistry*, 10:4, 321-340 (2003).
Stewart, J. M., and Young, J. D., *Solid Phase Peptide Synthesis*, 1984, 2 Ed., Pierce Chemical Company, Rockford, Illinois (book not provided).
Suto et al., *Anticancer Drug Des.*, 1991, vol. 6, 107-17.
Thompson, L. H. et al., *Mutat. Res.*, 2002, vol. 509, 49-78.
Uhlmann et al., *Chem. Rev.*, 1990, vol. 90, 543-584.
Virag and Szabo, "The Therapeutic Potential of Poly(ADP-Ribose) Polymerase Inhibitors," *Pharmacological Reviews*, vol. 54(3), (2002) 375-429.
Voinnet et al., *Nature*, 1997, vol. 389, 553.
Wang, Z.-Q. et al., *Genes Dev.*, 1997, vol. 11, 2347-58.
West, A.R. "Solid State Chemistry and its Applications" Wiley, New York, 358 and 365 (1988).
Wood et al., *Science*, 2001, vol. 291, 1284-89.
Dusemund, "Isochino [3,2-a]phthalazin-5,8-dione", *Arch. Pharm.*, (Weinhein) 1982, pp. 925-930. (English Abstract).

\* cited by examiner

*Primary Examiner*—James O. Wilson
*Assistant Examiner*—Paul V. Ward
(74) *Attorney, Agent, or Firm*—Michael Best & Friedrich LLP

(57) ABSTRACT

A method of treatment of a disease of the human or animal body mediated by PARP comprising administering to such a subject a therapeutically effective amount of a compound of formula:

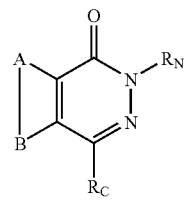

or an isomer, salt, solvate, chemically protected form, and prodrug thereof, wherein:
A and B together represent an optionally substituted, fused aromatic ring;
$R_C$ is represented by —L—$R_L$, where L is of formula:

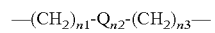

$$—(CH_2)_{n1}-Q_{n2}-(CH_2)_{n3}—$$

wherein $n_1$, $n_2$ and $n_3$ are each selected from 0, 1, 2 and 3, the sum of $n_1$, $n_2$ and $n_3$ is 1, 2 or 3 and Q is selected from O, S, NH, C(=O) or —$CR_1R_2$—, where $R_1$ and $R_2$ are independently selected from hydrogen, halogen or optionally substituted $C_{1-7}$ alkyl, or may together with the carbon atom to which they are attached form a $C_{3-7}$ cyclic alkyl group, which may be saturated (a $C_{3-7}$ cycloalkyl group) or unsaturated (a $C_{3-7}$ cycloalkenyl group), or one of $R_1$ and $R_2$ may be attached to an atom in $R_L$ to form an unsaturated $C_{3-7}$ cycloalkenyl group which comprises the carbon atoms to which $R_1$ and $R_2$ are attached in Q, —$(CH_2)_{n3}$— (if present) and part of $R_L$;
and $R_L$ is optionally substituted $C_{5-20}$ aryl; and
$R_N$ is selected from hydrogen, optionally substituted $C_{1-7}$ alkyl, $C_{3-20}$ heterocyclyl, and $C_{5-20}$ aryl, hydroxy, ether, nitro, amino, amido, thiol, thioether, sulfoxide and sulfone.

8 Claims, 19 Drawing Sheets

126

129

132

141

151

186

191

211

248

139

163

192

138

142

193

194

164

165

276

277

159

160

166                        167

227                        169

170                        171

172                        233

278                        640

641 642

643 644

645 646

647 648

649 650

651

652

653

654

655

656

657

658

659

667

668

669

670

671

672

673

674

675

676

677

678

679

680

681

682

683

684

685

686

687

688

691

692

693

694

697

698

699

700

701

702

703

704

705

706

215

216

206

253

254

265

179

212

289

290

291

292

293

294

295

296

298 299

300 601

602 603

604 605

607

608

609

610

611

612

613

614

615

616

617

618

619

620

621

622

623

624

625

626

627

628

629

630

631

213

239
180

222
247

241
198

204
202

131

177

178

249

279

145

90

91

92

93

266

283

284

285

PHTHALAZINONE DERIVATIVES

This application claims priority to United Kingdom Patent Application Number 0026505.8 filed Oct. 30, 2000, U.S. Provisional Application No. 60/245,662 filed Nov. 6, 2000, and U.S. Provisional Application No. 60/275,066, filed Mar. 12, 2001, the contents of which are incorporated herein by reference in their entirety.

The present invention relates to phthalazinone derivatives, and their use as pharmaceuticals. In particular, the present invention relates to the use of these compounds to inhibit the activity of the enzyme poly (ADP-ribose)polymerase, also known as poly(ADP-ribose)synthase and poly ADP-ribosyltransferase, and commonly referred to as PARP.

The mammalian enzyme PARP (a 113-kDa multidomain protein) has been implicated in the signalling of DNA damage through its ability to recognize and rapidly bind to DNA single or double strand breaks (D'Amours et al, 1999, Biochem. J. 342: 249–268).

Several observations have led to the conclusion that PARP participates in a variety of DNA-related functions including gene amplification, cell division, differentiation, apoptosis, DNA base excision repair and also effects on telomere length and chromosome stability (d'Adda di Fagagna et al, 1999, Nature Gen., 23(1): 76–80).

Studies on the mechanism by which PARP modulates DNA repair and other processes has identified its importance in the formation of poly (ADP-ribose) chains within the cellular nucleus (Althaus, F. R. and Richter, C., 1987, ADP-Ribosylation of Proteins: Enzymology and Biological Significance, Springer-Verlag, Berlin). The DNA-bound, activated PARP utilizes NAD to synthesize poly (ADP-ribose) on a variety of nuclear target proteins, including topoisomerase, histones and PARP itself (Rhun et al, 1998, Biochem. Biophys. Res. Commun., 245: 1–10).

Poly (ADP-ribosyl)ation has also been associated with malignant transformation. For example, PARP activity is higher in the isolated nuclei of SV40-transformed fibroblasts, while both leukemic cells and colon cancer cells show higher enzyme activity than the equivalent normal leukocytes and colon mucosa (Miwa et al, 1977, Arch. Biochem. Biophys. 181: 313–321; Burzio et al, 1975, Proc. Soc. Exp. Bioi. Med. 149: 933–938; and Hirai et al, 1983, Cancer Res. 43: 3441–3446).

A number of low-molecular-weight inhibitors of PARP have been used to elucidate the functional role of poly (ADP-ribosyl)ation in DNA repair. In cells treated with alkylating agents, the inhibition of PARP leads to a marked increase in DNA-strand breakage and cell killing (Durkacz et al, 1980, Nature 283: 593–596; Berger, N. A., 1985, Radiation Research, 101: 4–14).

Subsequently, such inhibitors have been shown to enhance the effects of radiation response by suppressing the repair of potentially lethal damage (Ben-Hur et al, 1984, British Journal of Cancer, 49 (Suppl. VI): 34–42; Schlicker et al, 1999, Int. J. Radiat. Bioi., 75: 91–100). PARP inhibitors have been reported to be effective in radio sensitising hypoxic tumour cells (U.S. Pat. Nos. 5,032,617; 5,215,738 and 5,041,653).

Furthermore, PARP knockout (PARP −/−) animals exhibit genomic instability in response to alkylating agents and γ-irradiation (Wang et al, 1995, genes Dev., 9: 509–520; Menissier de Murcia et al, 1997, Proc. Natl. Acad. Sci. USA, 94: 7303–7307).

A role for PARP has also been demonstrated in certain vascular diseases, septic shock, ischaemic injury and neurotoxicity (Cantoni et al, 1989, Biochim. Biophys. Acta, 1014: 1–7; Szabo, et al, 1997, J. Clin.lnvest., 100: 723-735). Oxygen radical DNA damage that leads to strand breaks in DNA, which are subsequently recognised by PARP, is a major contributing factor to such disease states as shown by PARP inhibitor studies (Cosi et al, 1994, J. Neurosci. Res., 39: 38–46; Said et al, 1996, Proc. Natl. Acad. Sci. U.S.A., 93: 4688–4692). More recently, PARP has been demonstrated to play a role in the pathogenesis of haemorrhagic shock (Liaudet et al, 2000, Proc. Natl. Acad. Sci. U.S.A., 97(3): 10203–10208).

It has also been demonstrated that efficient retroviral infection of mammalian cells is blocked by the inhibition of PARP activity. Such inhibition of recombinant retroviral vector infections was shown to occur in various different cell types (Gaken et al, 1996, J. Virology, 70(6): 3992–4000). Inhibitors of PARP have thus been developed for the use in anti-viral therapies and in cancer treatment (WO91/18591).

Moreover, PARP inhibition has been speculated to delay the onset of aging characteristics in human fibroblasts (Rattan and Clark, 1994, Biochem. Biophys. Res. Comm., 201 (2): 665–672). This may be related to the role that PARP plays in controlling telomere function (d'Adda di Fagagna et al, 1999, Nature Gen., 23(1): 76–80).

U.S. Pat. No. 5,874,444 discloses a number of PARP inhibitors, amongst which is 1(2H)-phthalazinone (100):

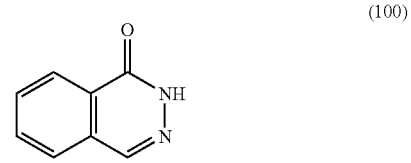

The present inventors have now discovered that certain derivatives of 1(2H)-phthalazinone and related compounds exhibit inhibition of the activity of PARP.

Accordingly, the first aspect of the present invention provides a method of treatment of a disease of the human or animal body mediated by PARP comprising administering to such a subject a therapeutically effective amount of a compound of formula:

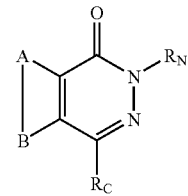

or an isomer, salt, solvate, chemically protected form, and prodrug thereof, wherein:

A and B together represent an optionally substituted, fused aromatic ring;

$R_C$ is represented by -L-$R_L$, where L is of formula:

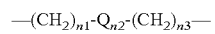

wherein $n_1$, $n_2$ and $n_3$ are each selected from 0, 1, 2 and 3, the sum of $n_1$, $n_2$ and $n_3$ is 1, 2 or 3 and Q is selected from O, S, NH, C(=O) or —$CR_1R_2$—, where $R_1$ and $R_2$ are independently selected from hydrogen, halogen or optionally substituted $C_{1-7}$ alkyl, or may together with the carbon atom to which they are attached form a $C_{3-7}$ cyclic alkyl group, which may be saturated (a $C_{3-7}$ cycloalkyl group) or unsaturated (a $C_{3-7}$ cycloalkenyl group), or one of $R_1$ and $R_2$ may be attached to an atom in $R_L$ to form an unsaturated $C_{3-7}$ cycloalkenyl group which comprises the carbon atoms to which $R_1$ and $R_2$ are attached in Q, —$(CH_2)_{n3}$— (if present) and part of $R_L$;

and $R_L$ is optionally substituted $C_{5-20}$ aryl; and $R_N$ is selected from hydrogen, optionally substituted $C_{1-7}$ alkyl, $C_{3-20}$ heterocyclyl, and $C_{5-20}$ aryl, hydroxy, ether, nitro, amino, amido, thiol, thioether, sulfoxide and sulfone.

A second aspect of the present invention relates to a compound of the formula:

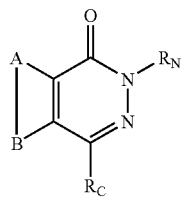

or an isomer, salt, solvate, chemically protected form, and prodrug thereof, wherein:

A and B together represent an optionally substituted, fused aromatic ring;

$R_C$ is —$CH_2$—$R_L$;

$R_L$ is optionally substituted phenyl; and $R_N$ is hydrogen.

A third aspect of the present invention relates to a pharmaceutical composition comprising a compound of the second aspect and a pharmaceutically acceptable carrier or diluent.

Further aspects of the invention provide for a method of treatment as described in the first aspect of the invention, wherein the disease mediated by PARP is: vascular disease; septic shock; ischaemic injury; neurotoxicity; haemorraghic shock; or viral infection.

A further aspect of the invention provides a method of cancer therapy for the human or animal body comprising administering to such a subject a therapeutically effective amount of a compound as described in the first aspect in combination with chemotherapy or radiation therapy.

Another further aspect of the invention provides a method of potentiating tumour cells for treatment with ionising radiation or chemotherapeutic agents comprising administering to said cells a compound as described in the first aspect of the invention. Such a method may be practised in vivo or in vitro.

It is preferred that when a compound is administered it is done so in the form of a pharmaceutical composition.

DEFINITIONS

Figure 1:
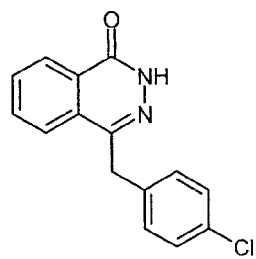
FIGS. 1 to 19 show compounds according to the present invention.
Figure 1:
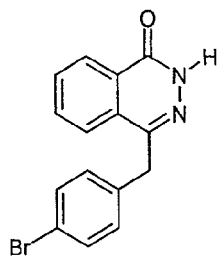
Figure 1:
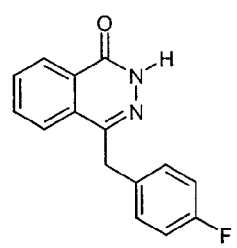
Figure 1:
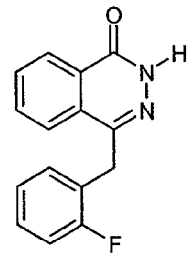
Figure 1:
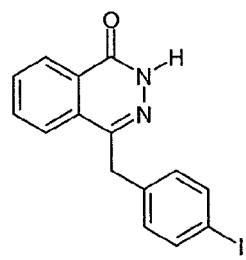
Figure 1:
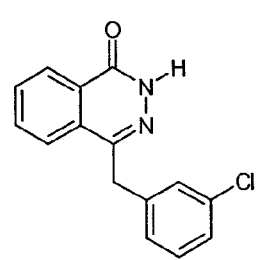
Figure 1:
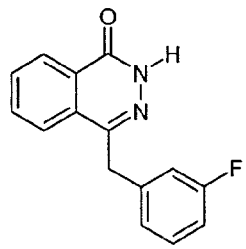
Figure 1:
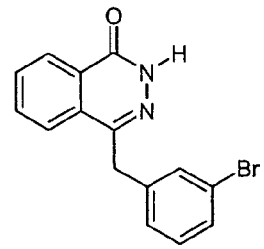
Figure 1:
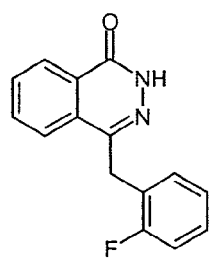
Figure 2:
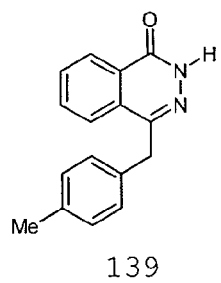
Figure 2:
Figure 2:
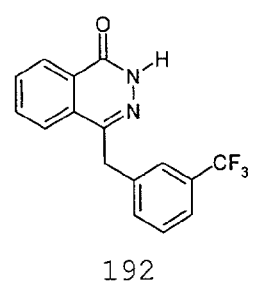
Figure 2:
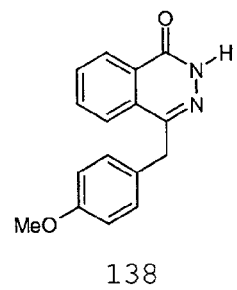
Figure 2:
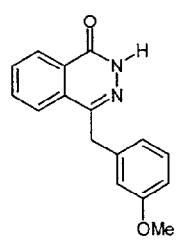
Figure 2:
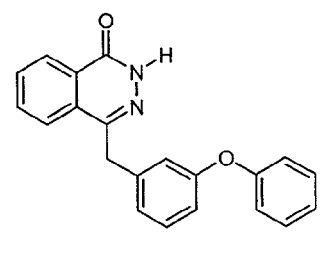
Figure 2:
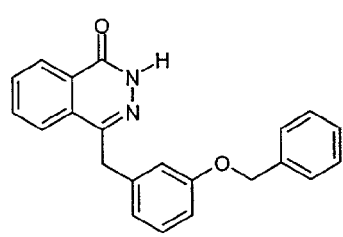
Figure 2:
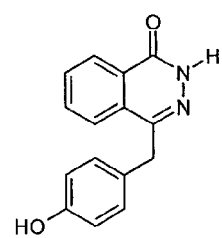
Figure 2:
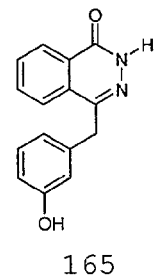
Figure 3:
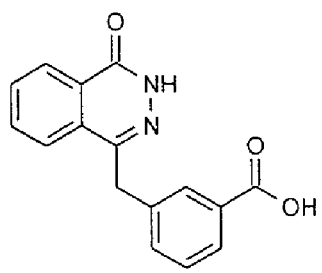
Figure 3:
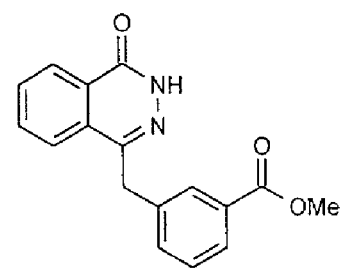
Figure 3:
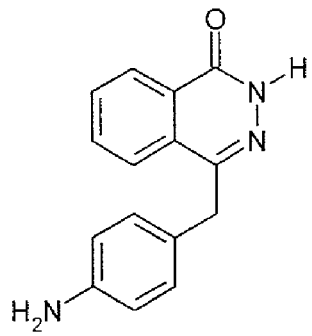
Figure 3:
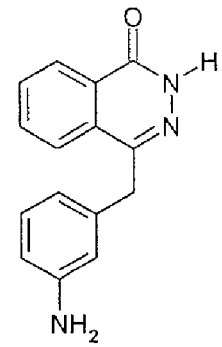
Figure 4:
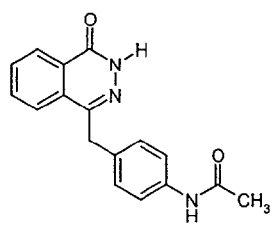
Figure 4:
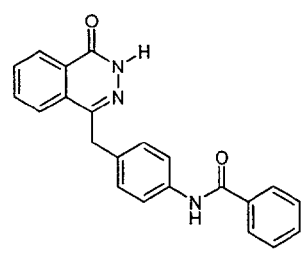
Figure 4:
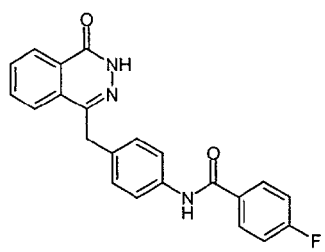
Figure 4:
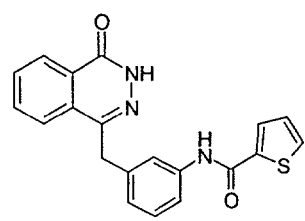
Figure 4:
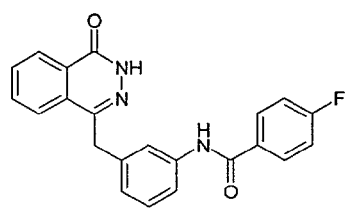
Figure 4:
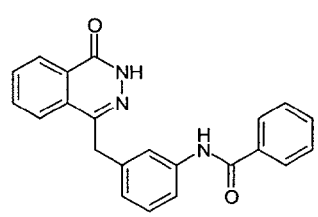
Figure 4:
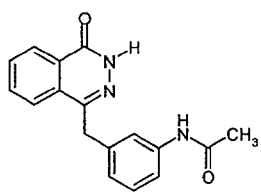
Figure 4:
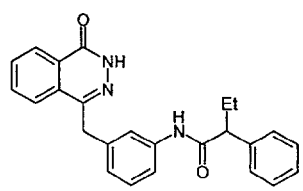
Figure 4:
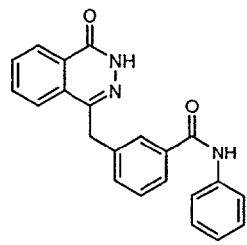
Figure 4:
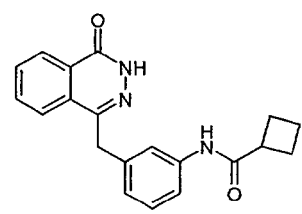
Figure 5:
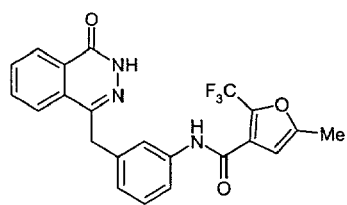
Figure 5:
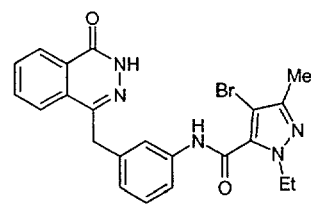
Figure 5:
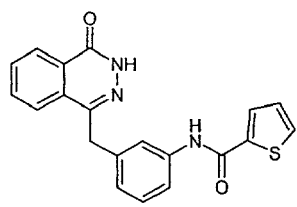
Figure 5:
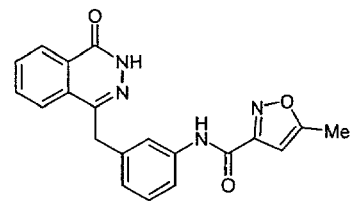
Figure 5:
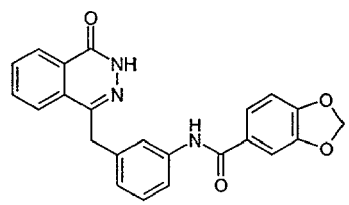
Figure 5:
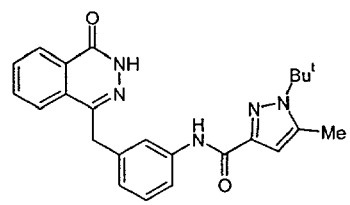
Figure 5:
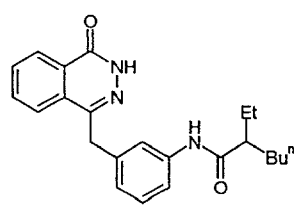
Figure 5:
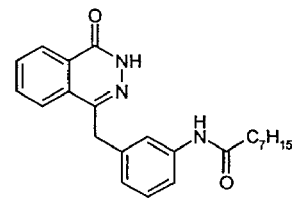
Figure 5:
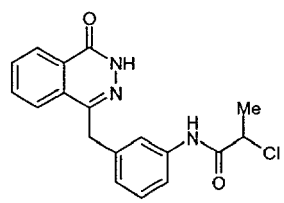
Figure 5:
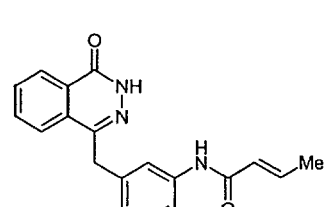
Figure 6:
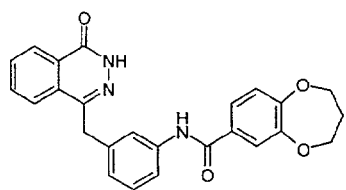
Figure 6:
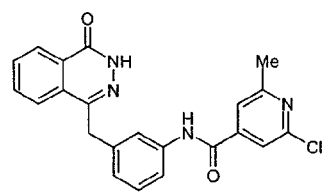
Figure 6:
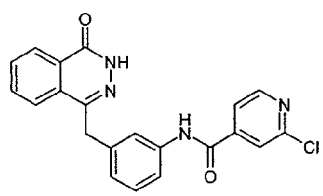
Figure 6:
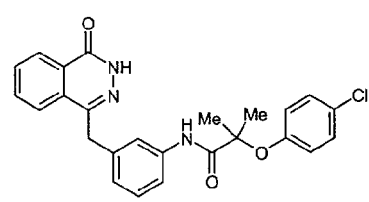
Figure 6:
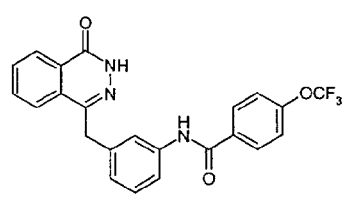
Figure 6:
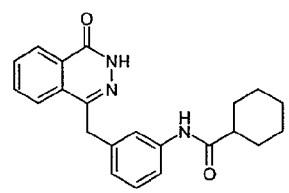
Figure 6:
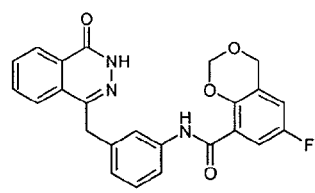
Figure 6:
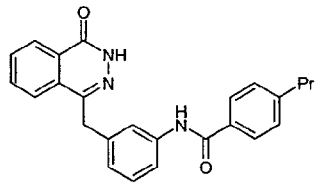
Figure 6:
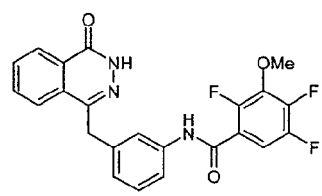
Figure 6:
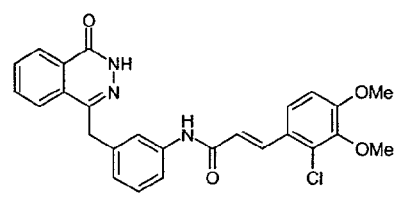
Figure 7:
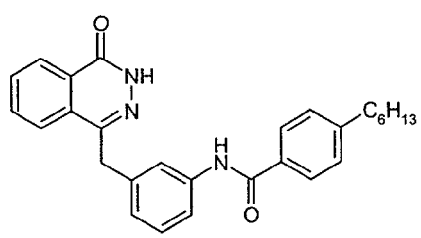
Figure 7:
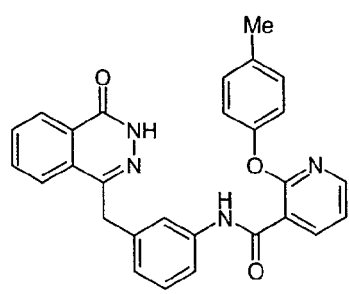
Figure 7:
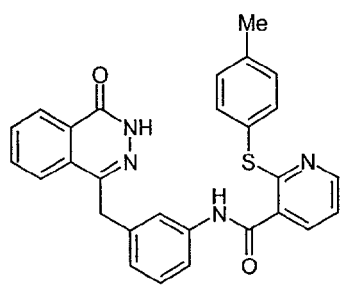
Figure 7:
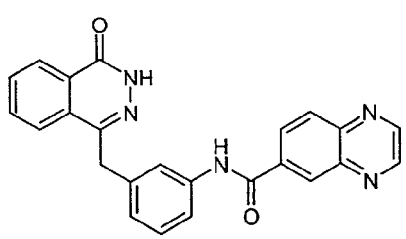
Figure 7:
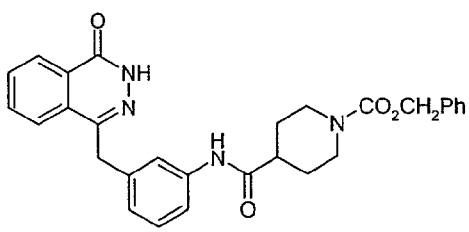
Figure 7:
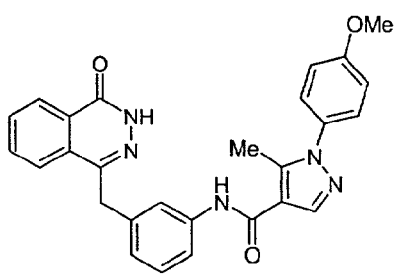
Figure 7:
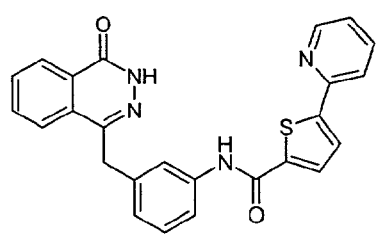
Figure 7:
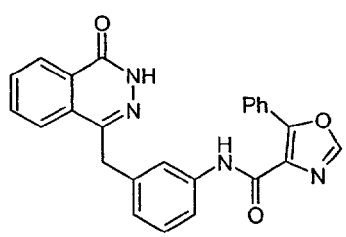
Figure 7:
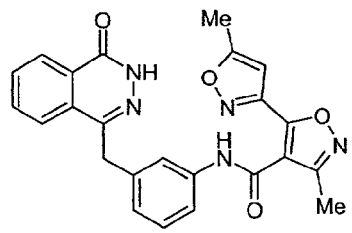
Figure 7:
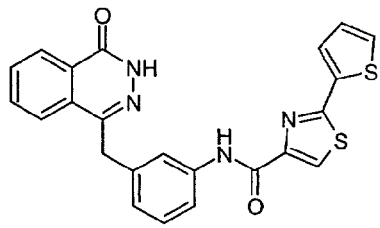
Figure 8:
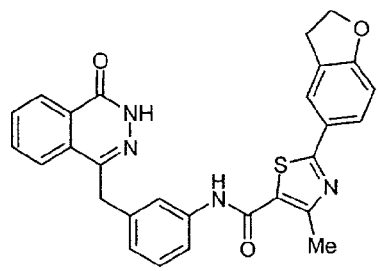
Figure 8:
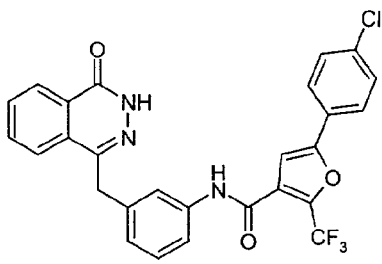
Figure 8:
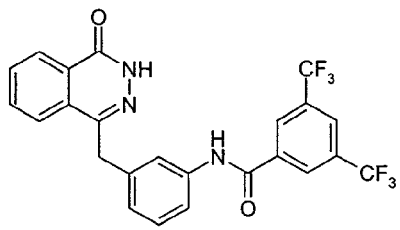
Figure 8:
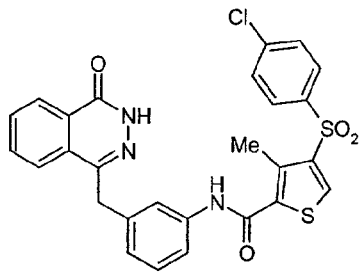
Figure 8:
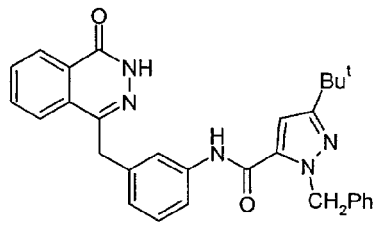
Figure 8:
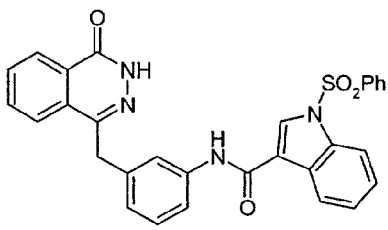
Figure 8:
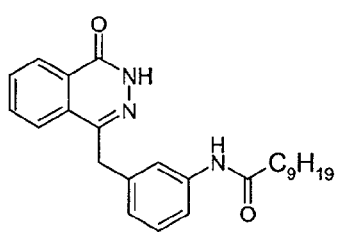
Figure 8:
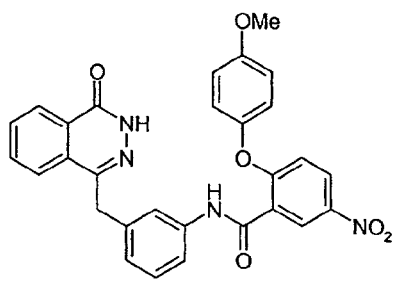
Figure 8:
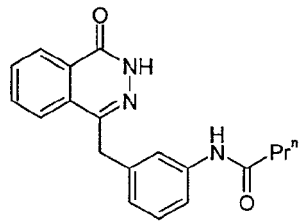
Figure 9:
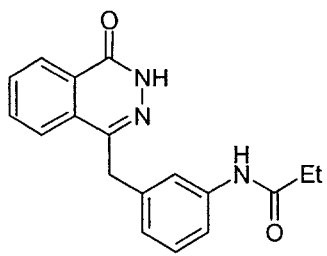
Figure 9:
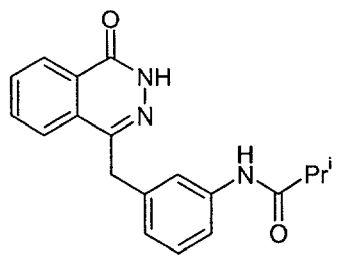
Figure 9:
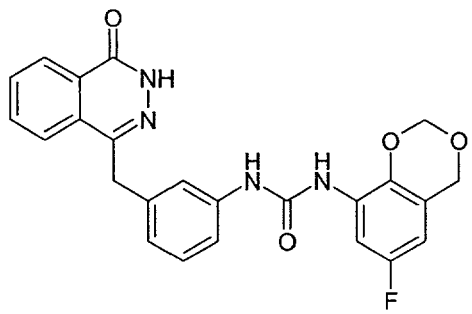
Figure 9:
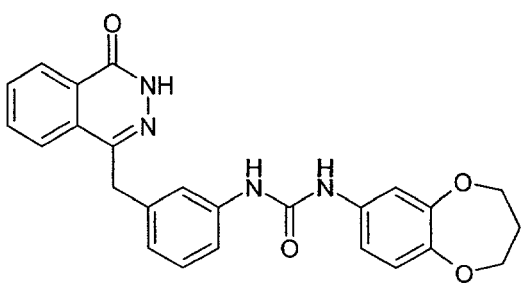
Figure 9:
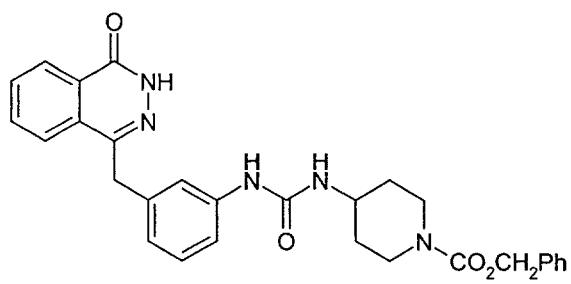
Figure 9:
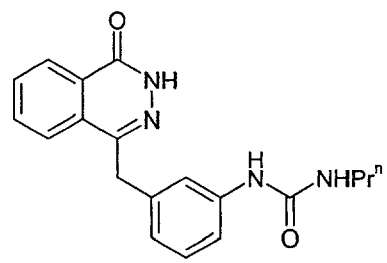
Figure 9:
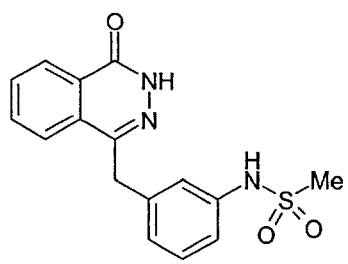
Figure 10:
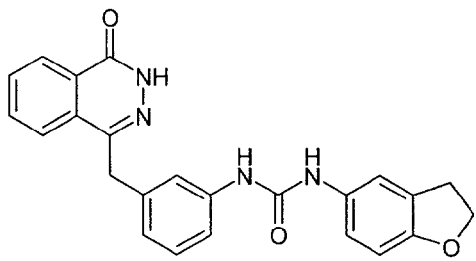
Figure 10:
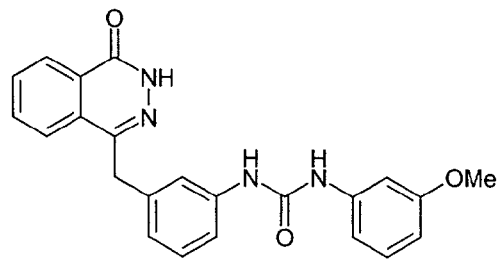
Figure 10:
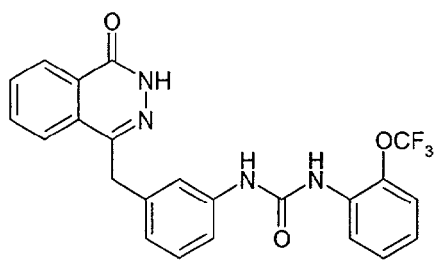
Figure 10:
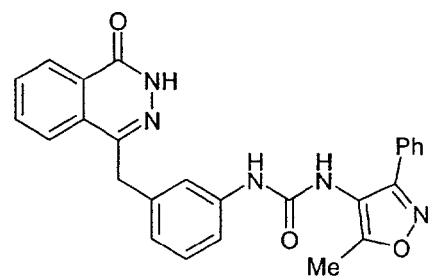
Figure 10:
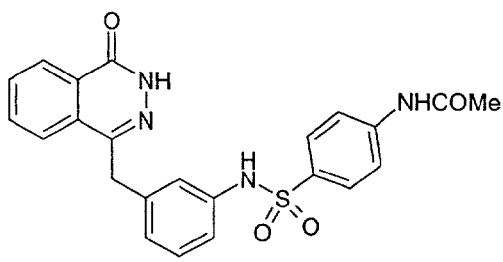
Figure 10:
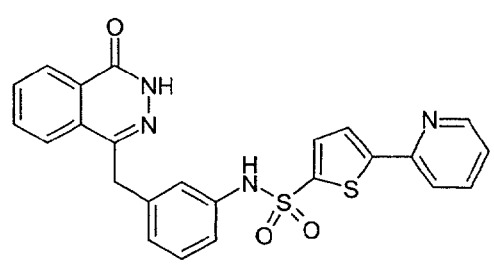
Figure 10:
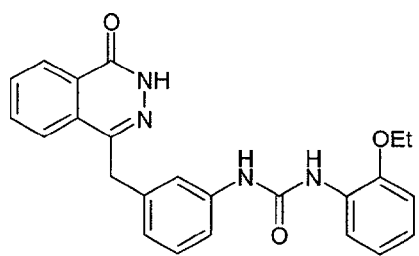
Figure 11:
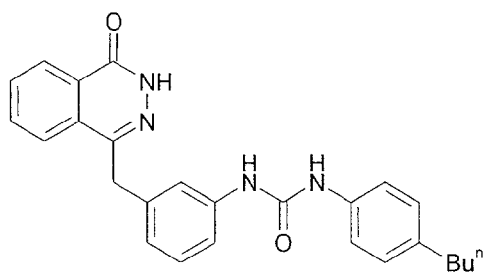
Figure 11:
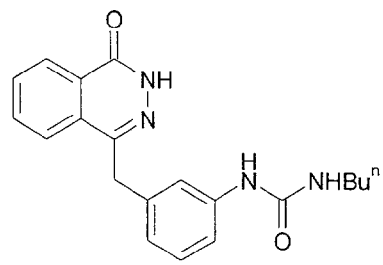
Figure 11:
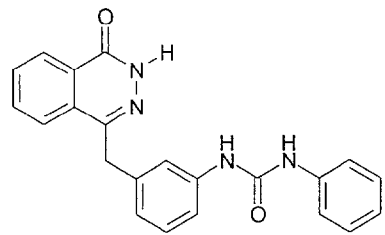
Figure 11:
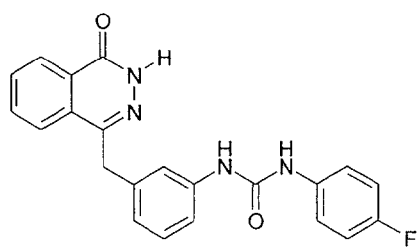
Figure 11:
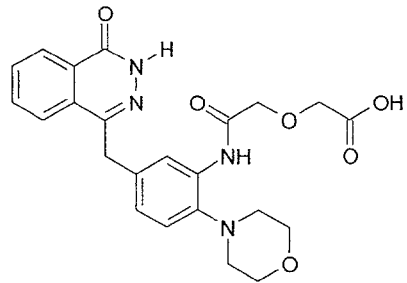
Figure 11:
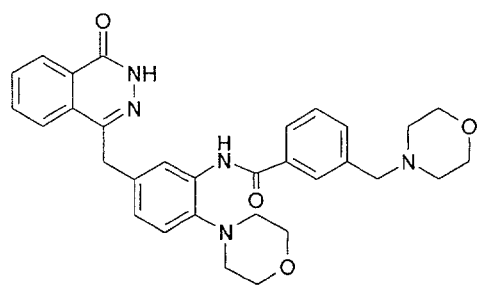
Figure 11:
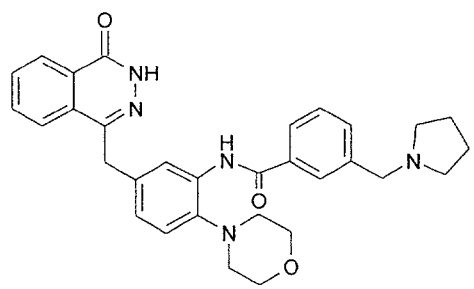
Figure 11:
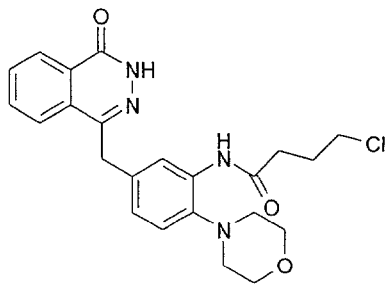
Figure 12:
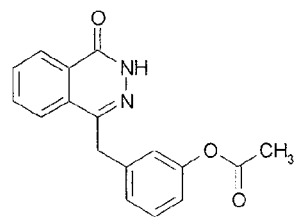
Figure 12:
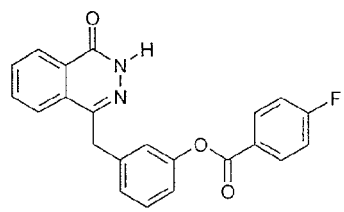
Figure 12:
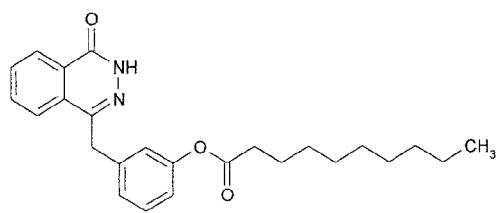
Figure 12:
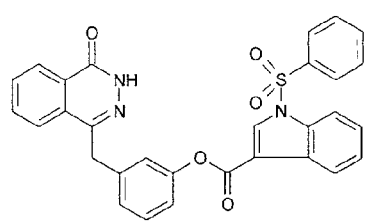
Figure 12:
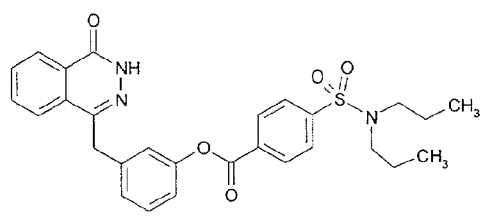
Figure 12:
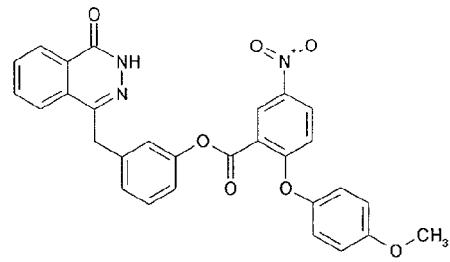
Figure 12:
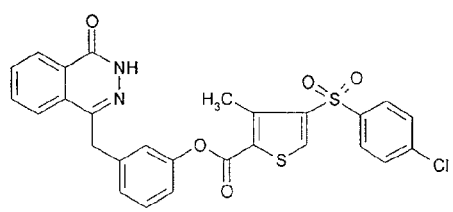
Figure 12:
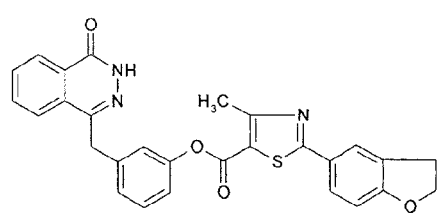
Figure 12:
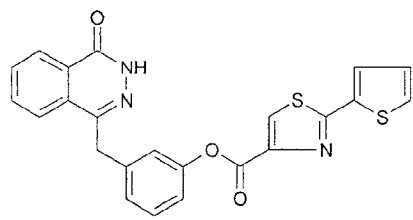
Figure 12:
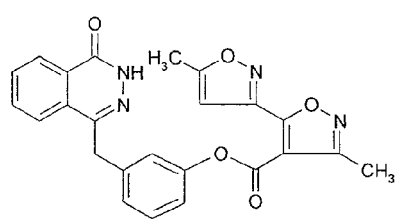
Figure 13:
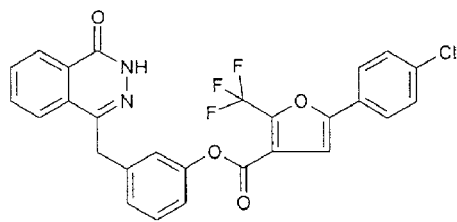
Figure 13:
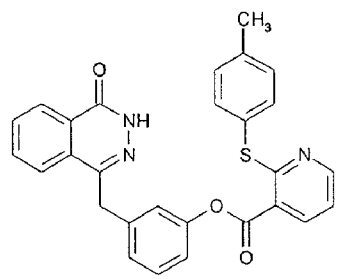
Figure 13:
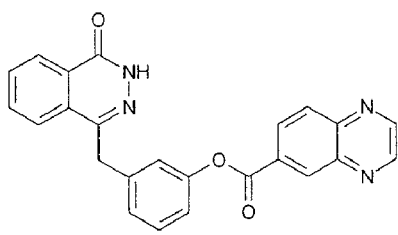
Figure 13:
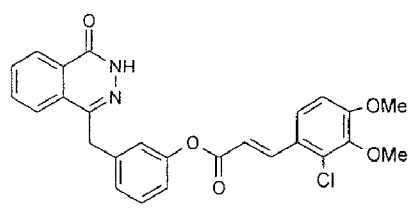
Figure 13:
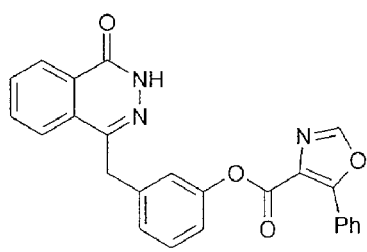
Figure 13:
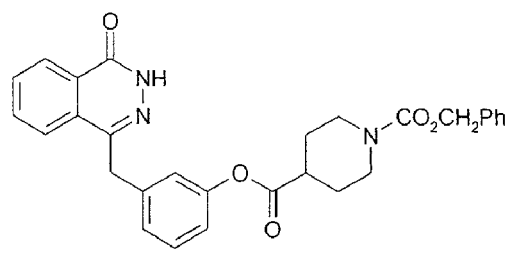
Figure 13:
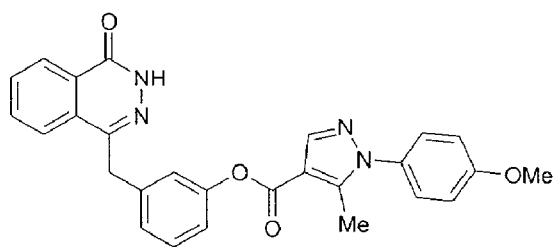
Figure 13:
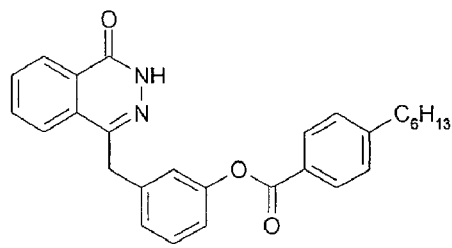
Figure 14:
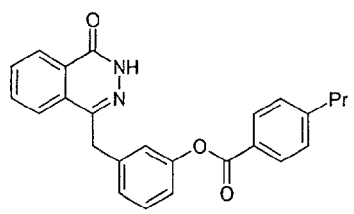
Figure 14:
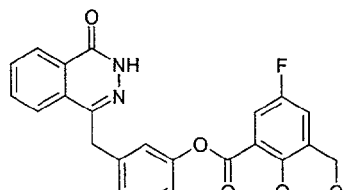
Figure 14:
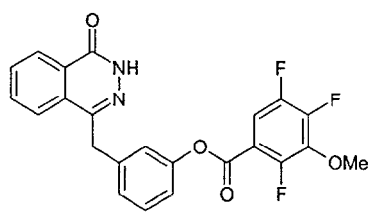
Figure 14:
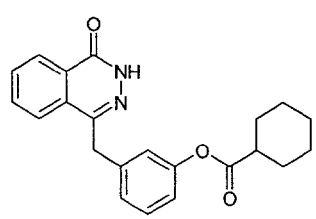
Figure 14:
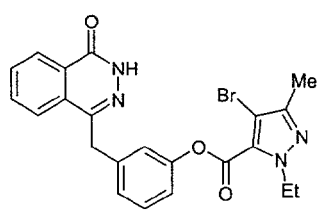
Figure 14:
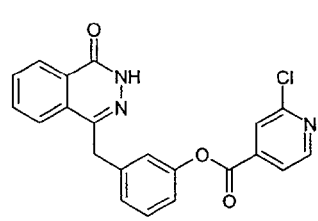
Figure 14:
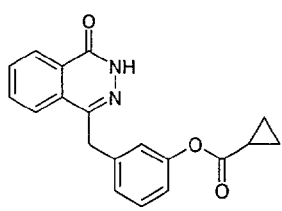
Figure 14:
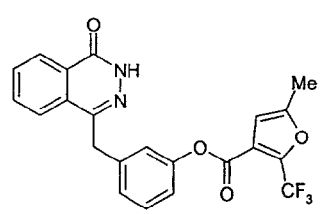
Figure 14:
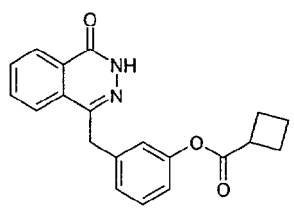
Figure 14:
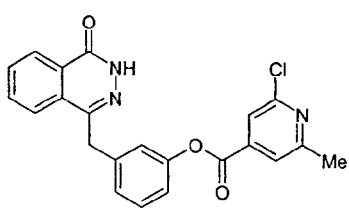
Figure 15:
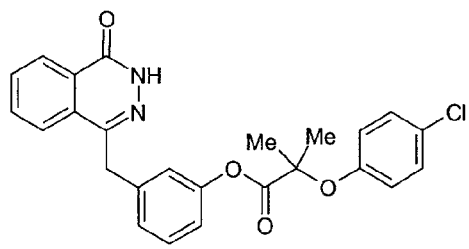
Figure 15:
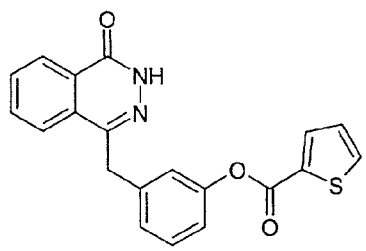
Figure 15:
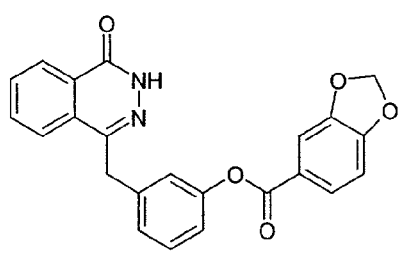
Figure 15:
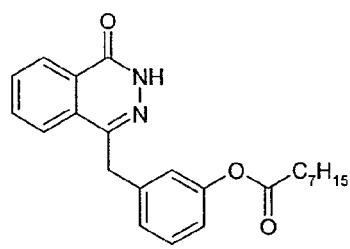
Figure 15:
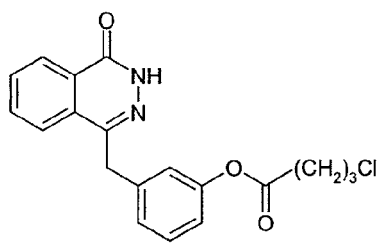
Figure 15:
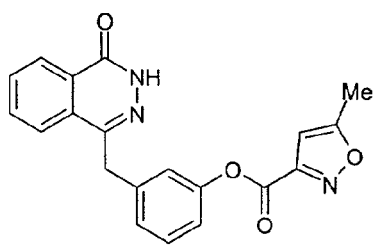
Figure 15:
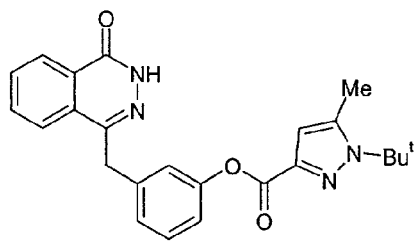
Figure 15:
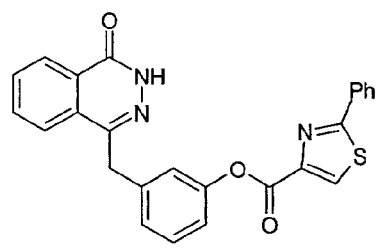
Figure 15:
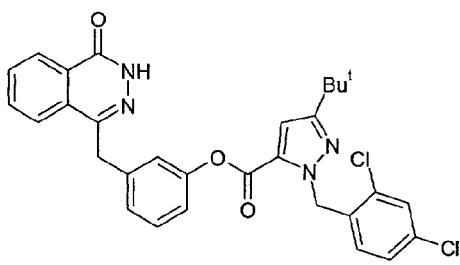
Figure 15:
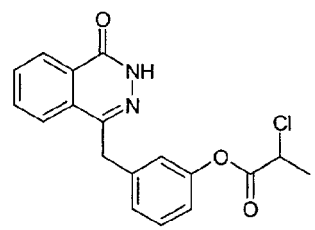
Figure 16:
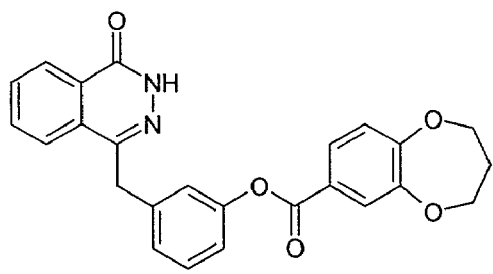
Figure 16:
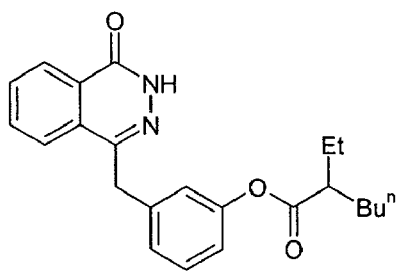
Figure 16:
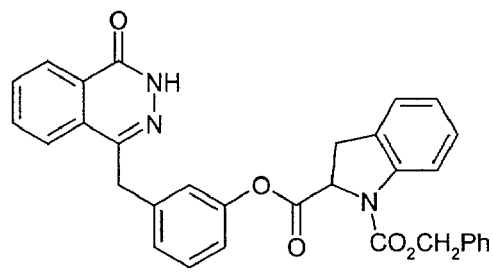
Figure 16:
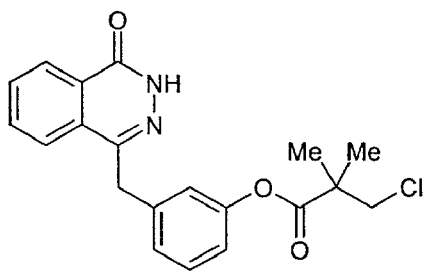
Figure 16:
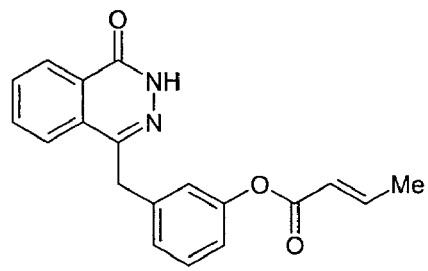
Figure 16:
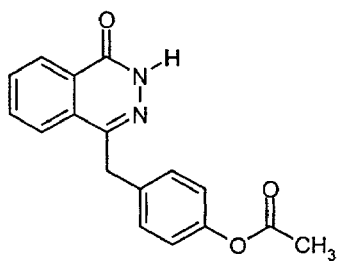
Figure 17:
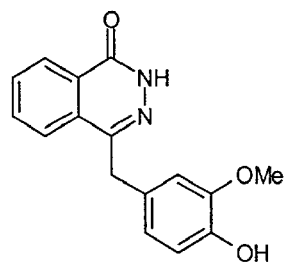
Figure 17:
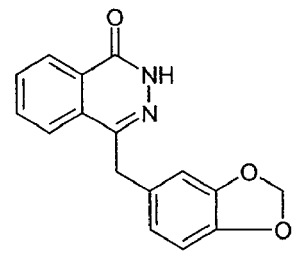
Figure 17:
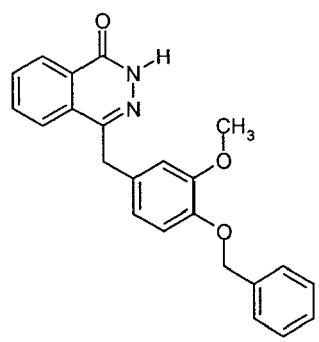
Figure 17:
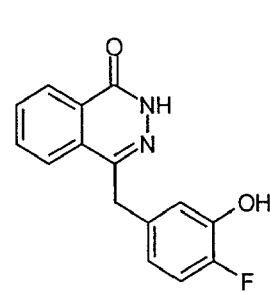
Figure 17:
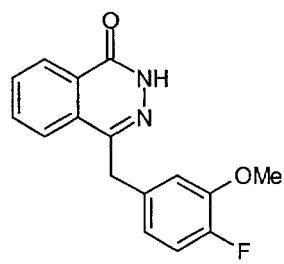
Figure 17:
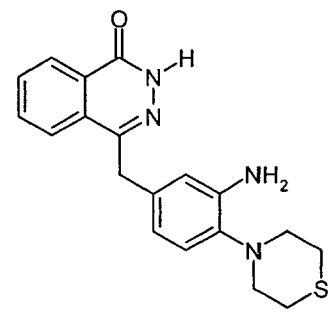
Figure 17:
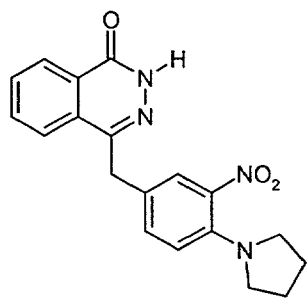
Figure 17:
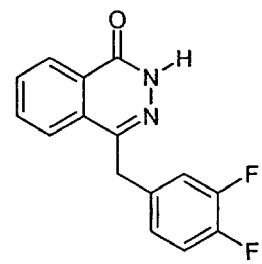
Figure 18:
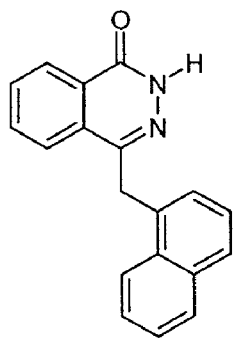
Figure 18:
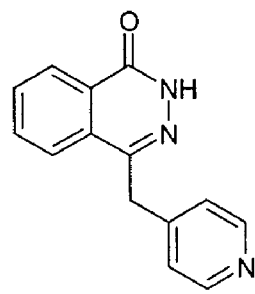
Figure 18:
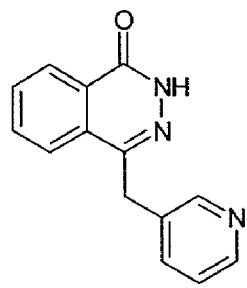
Figure 18:
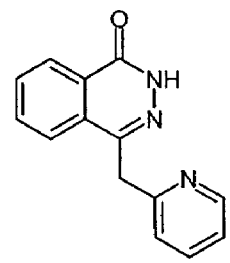
Figure 18:
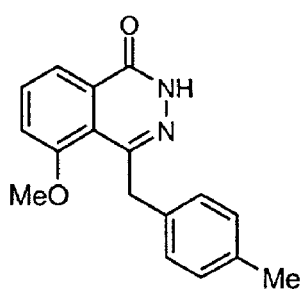
Figure 18:
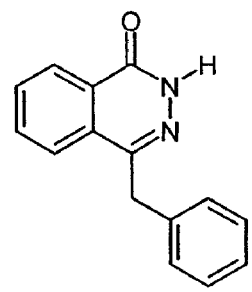
Figure 19:
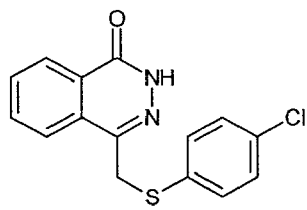
Figure 19:
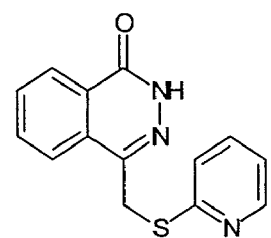
Figure 19:
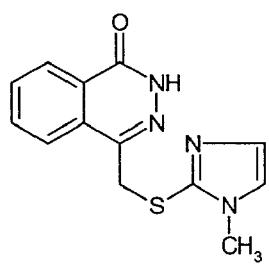
Figure 19:
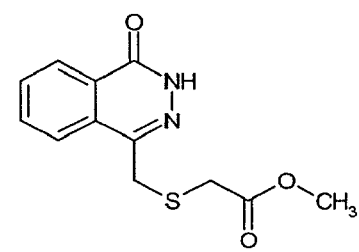
Figure 19:
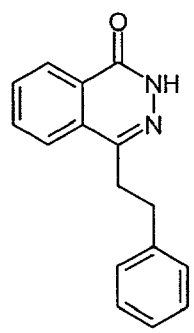
Figure 19:
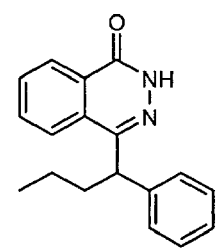
Figure 19:
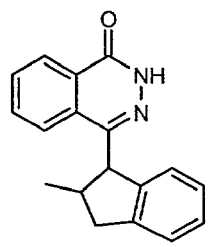
Figure 19:
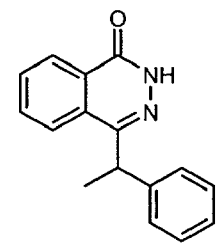

The term "aromatic ring" is used herein in the conventional sense to refer to a cyclic aromatic structure, that is, a cyclic structure having delocalised n-electron orbitals.

The aromatic ring fused to the main core, i.e. that formed by -A-B—, may bear further fused aromatic rings (resulting in, e.g. naphthyl or anthracenyl groups). The aromatic ring(s) may comprise solely carbon atoms, or may comprise carbon atoms and one or more heteroatoms, including but not limited to, nitrogen, oxygen, and sulfur atoms. The aromatic ring(s) preferably have five or six ring atoms.

The aromatic ring(s) may optionally be substituted. If a substituent itself comprises an aryl group, this aryl group is not considered to be a part of the aryl group to which it is attached. For example, the group biphenyl is considered herein to be a phenyl group (an aryl group comprising a single aromatic ring) substituted with a phenyl group. Similarly, the group benzylphenyl is considered to be a phenyl group (an aryl group comprising a single aromatic ring) substituted with a benzyl group.

In one group of preferred embodiments, the aromatic group comprises a single aromatic ring, which has five or six ring atoms, which ring atoms are selected from carbon, nitrogen, oxygen, and sulfur, and which ring is optionally substituted. Examples of these groups include benzene, pyrazine, pyrrole, thiazole, isoxazole, and oxazole. 2-Pyrone can also be considered to be an aromatic ring, but is less preferred.

If the aromatic ring has six atoms, then preferably at least four, or even five or all, of the ring atoms are carbon.

The other ring atoms are selected from nitrogen, oxygen and sulphur, with nitrogen and oxygen being preferred. Suitable groups include a ring with: no hetero atoms (benzene); one nitrogen ring atom (pyridine); two nitrogen ring atoms (pyrazine, pyrimidine and pyridazine); one oxygen ring atom (pyrone); and one oxygen and one nitrogen ring atom (oxazine).

If the aromatic ring has five ring atoms, then preferably at least three of the ring atoms are carbon. The remaining ring atoms are selected from nitrogen, oxygen and sulphur. Suitable rings include a ring with: one nitrogen ring atom (pyrrole); two nitrogen ring atoms (imidazole, pyrazole); one oxygen ring atom (furan); one sulphur ring atom (thiophene); one nitrogen and one sulphur ring atom (thiazole); and one nitrogen and one oxygen ring atom (isoxazole or oxazole).

The aromatic ring may bear one or more substituent groups at any available ring position. These substituents are selected from halo, nitro, hydroxy, ether, thiol, thioether, amino, $C_{1-7}$ alkyl, $C_{3-20}$ heterocyclyl and $C_{5-20}$ aryl. The aromatic ring may also bear one or more substituent groups which together form a ring. In particular these may be of formula —$(CH_2)_m$— or —O—$(CH_2)_p$—O—, where m is 2, 3, 4 or 5 and p is 1, 2 or 3.

$C_{1-7}$ alkyl: The term "$C_{1-7}$ alkyl" as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$ alkyl groups include, but are not limited to, methyl, ethyl, n-propyl, n-butyl, and n-pentyl (amyl).

Examples of (unsubstituted) saturated branched $C_{1-7}$ alkyl groups include, but are not limited to, iso-propyl, iso-butyl, sec-butyl, tert-butyl, and neo-pentyl.

Examples of saturated alicyclic (carbocyclic) $C_{1-7}$ alkyl groups (also referred to as "$C_{3-7}$ cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$ alkyl groups which have one or more carbon-carbon double bonds (also referred to as "$C_{2-7}$ alkenyl" groups) include, but are not limited to, ethenyl (vinyl, —CH=CH$_2$), 2-propenyl (allyl, —CH$_2$—CH=CH$_2$), isopropenyl (—C(CH$_3$)=CH$_2$), butenyl, pentenyl, and hexenyl.

Examples of (unsubstituted) unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$ cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl" as used herein, pertains to a monovalent moiety obtained by removing a hydrogen atom from a ring atom of a non-aromatic $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, azetine, pyrrolidine, pyrroline, piperidine, dihydropyridine, tetrahydropyridine, and dihydropyrrole (azoline).

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, and pyran. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulfur ring atom include, but are not limited to, those derived from thiolane (tetrahydrothiophene, thiane) and tetrahydrothiopyran.

Examples of $C_{3-20}$ heterocyclyl groups having two oxygen ring atoms include, but are not limited to, those derived from dioxane, for example 1,3-dioxane and 1,4-dioxane. Examples of $C_{3-20}$ heterocyclyl groups having two nitrogen ring atoms include, but are not limited to, those derived from diazolidine (pyrazolidine), pyrazoline, imidazolidine, imidazoline, and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroiosoxazole, morpholine, tetrahydrooxazine, dihydrooxazine, and oxazine.

Examples of $C_{3-20}$ heterocyclyl groups having one oxygen ring atom and one sulfur ring atom include, but are not limited to, those derived from oxathiolane and oxathiane.

Examples of $C_{3-20}$ heterocyclyl groups having one nitrogen ring atom and one sulfur ring atom include, but are not limited to, those derived from thiazoline, thiazolidine, and thiomorpholine.

Other examples of $C_{3-20}$ heterocyclyl groups include, but are not limited to, oxadiazine.

If the $C_{3-20}$ heterocyclyl is substituted, the substituents are on carbon, or nitrogen (if present), atoms.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e., $C_{5-20}$ carboaryl groups) include, but are not limited to, those derived from benzene (i.e., phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

The heteroaryl group may be bonded via a carbon or hetero ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —NO$_2$.

Cyano (nitrile, carbonitrile): —CN.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, perhydrodiazepino, morpholino, and thiomorpholino. The cylic amino groups may be substituted on their ring by any of the substituents defined here, for example carboxy, carboxylate and amido. A particular form of amino group is where one of R$^1$ and R$^2$ is a sulfone (—S(=O)$_2$R), where R is a sulfone substituent, and this group can be termed a sulfonamido group. Examples of sulfonamido groups include, but are not limited to, —NHS(=O)$_2$CH$_3$, —NHS(=O)$_2$Ph and —NHS(=O)$_2$C$_6$H$_4$F.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably H or a C$_{1-7}$ alkyl group, most preferably H, and R$^2$ is an acyl substituent, for example, a C$_{1-7}$ alkyl group, a C$_{3-20}$ heterocyclyl group, or a C$_{5-20}$ aryl group, preferably a C$_{1-7}$ alkyl group. Examples of acylamide groups include, but are not limited to, —NHC(=O)CH$_3$, —NHC(=O)CH$_2$CH$_3$, and —NHC(=O)Ph. One particular form of acylamido group is where R$^2$ is an amino group (—NR$^3$R$^4$), where R$^3$ and R$^4$ are independently amino substituents, as this group can be termed an ureido group. Example of ureido groups include, but are not limited to —NHC(=O) NHCH$_3$, —NHC(=O)NHCH$_2$CH$_3$, and —NHC(=O)NHPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a C$_{1-7}$ alkyl group, a C$_{3-20}$ heterocyclyl group, or a C$_{5-20}$ aryl group, preferably a C$_{1-7}$ alkyl group. Examples of sulfoxide groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

As mentioned above, the groups that form the above listed substituent groups, e.g. C$_{1-7}$ alkyl, C$_{3-20}$ heterocyclyl and C$_{5-20}$ aryl, may themselves be substituted. Thus, the above definitions cover substituent groups which are substituted.

Substituents Form a Ring

It is possible that a substituent on a ring which forms part of R$_C$ and a substituent on the fused aromatic ring (represented by -A-B—), may together form an intra ring link, thus forming a further cyclic structure in the compound.

The substituent on the aromatic ring that forms the intra ring link is preferably on the atom adjacent the central moiety (i.e. at the α-position).

The substituent on R$_C$ that forms the intra ring link is preferably on the atom which is one atom away from the atom which is bound to the central moiety.

The link between the two rings may be a single bond, or may be of the formula:

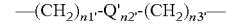

—(CH$_2$)$_{n1'}$-Q'$_{n2'}$-(CH$_2$)$_{n3'}$— wherein n1', n2' and n3' are each selected from 0, 1, 2 and 3 and the sum of n1', n2' and n3' is less than or equal to 3. Q' can be O, S, NH or C(=O).

Further Preferences

The following preferences can apply to each aspect of the present invention, where applicable.

In the present invention, the fused aromatic ring(s) represented by -A-B— preferably consist of solely carbon ring atoms, and thus may be benzene, naphthalene, and is more preferably benzene. As described above, these rings may be substituted, but in some embodiments are preferably unsubstituted.

R$_N$ is preferably selected from hydrogen, and amido. In one embodiment, R$_N$ is preferably amido, where one amido substituent is phenyl, optionally substituted by fluorine, preferably in the para position. In another embodiment, R$_N$ is preferably H.

In L, it is preferred that each Q (if n2 is greater than 1) is selected from O, S, NH or C(=O).

L is preferably of formula:

—(CH$_2$)$_{n1}$-Q$_{n2}$-, where n1 is selected from 0, 1, 2 and 3 and n2 is selected from 0 and 1 (where the sum of n1 and n2 is 1, 2 or 3), and more preferably n2 is 0. n1 is preferably 1 or 2, more preferably 1. The most preferred option for L is —CH$_2$—.

If Q in L is —CR$_1$R$_2$—, then n2 is preferably 1. In one embodiment, R$_1$ is optionally substituted C$_{1-7}$ alkyl and R$_2$ is hydrogen. R$_1$ is more preferably optionally substituted $C_{1-4}$ alkyl, and most preferably unsubstituted $C_{1-4}$ alkyl. In another embodiment, $R_1$ and $R_2$, together with the carbon atom to which they are attached, form a saturated $C_{3-7}$ cyclic alkyl group, more preferably a $C_{5-7}$ cyclic alkyl group. In a further embodiment, $R_1$ is attached to an atom in $R_L$ to form an unsaturated $C_{3-7}$ cycloalkenyl group, more preferably a $C_{5-7}$ cycloalkenyl group, which comprises the carbon atoms to which $R_1$ and $R_2$ are attached in Q, —$(CH_2)_{n3}$— (if present) and part of $R_L$, and $R_2$ is hydrogen.

$R_L$ is preferably a benzene ring, naphthalene, pyridine or 1,3-benzodioxole, and more preferably a benzene ring.

When $R_L$ is a benzene ring, it is preferably substituted. The one or more substituents may be selected from: $C_{1-7}$ alkyl, more preferably methyl, $CF_3$; $C_{5-20}$ aryl; $C_{3-20}$ heterocyclyl; halo, more preferably fluoro; hydroxy; ether, more preferably methoxy, phenoxy, benzyloxy, and cyclopentoxy; nitro; cyano; carbonyl groups, such as carboxy, ester and amido; amino (including sulfonamido), more preferably —$NH_2$, —NHPh, and cycloamino groups, such as morpholino; acylamido, including ureido groups, where the acyl or amino substituent is preferably phenyl, which itself is optionally fluorinated; acyloxy; thiol; thioether; sulfoxide; sulfone.

In one group of embodiments, fluoro is particularly preferred as a substituent, along with substituents containing a phenyl, or fluorinated phenyl, component.

Preferred substituents of the benzene ring, when $R_L$ is phenyl, include:

(i) acylamido, wherein the amide substituent is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any of those listed above, but those of particular interest include $C_{1-7}$ alkyl and $C_{5-20}$ aryl groups, halo, ether, thioether and sulfone groups;

(ii) ureido, where one amine substituent is preferably hydrogen, and the other is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any of those listed above, but those of particular interest include $C_{1-7}$ alkyl, $C_{3-20}$ heterocyclyl and $C_{5-20}$ aryl groups, halo and ether groups;

(iii) sulfonamino, wherein the amine substituent is preferably hydrogen and the sulfone substituent is selected from $C_{1-7}$ alkyl, $C_{3-20}$ heterocyclyl, and $C_{5-20}$ aryl, more preferably $C_{17}$ alkyl and $C_{5-20}$ aryl, which groups are optionally further substituted. The optional substituents may be selected from any of those listed above, but those of particular interest include $C_{5-20}$ aryl groups and acylamido groups;

(iv) acyloxy, wherein the acyloxy substituent is selected from $C_{1-7}$ alkyl, $C_{3-20}$ heterocyclyl, and $C_{5-20}$ aryl, more preferably $C_{1-7}$ alkyl and $C_{5-20}$ aryl, which groups are optionally further substituted. The optional substituents may be selected from any of those listed above, but those of particular interest include $C_{1-7}$ alkyl and $C_{5-20}$ aryl groups, halo, ether, thioether, sulfone and nitro groups.

If A and B together represent a substituted fused aromatic ring, it is preferred that the substituent does not form an intra ring link with a substituent on a ring which forms part of $R_C$. Substituents in the five position are particularly preferred.

Where appropriate, the above preferences may be taken in combination with each other.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair that exists when RN is H, illustrated below:

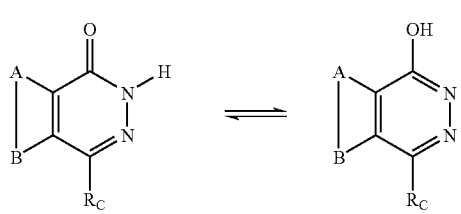

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C$_{1-7}$ alkyl (e.g. -Me, -Et); C$_{1-7}$aminoalkyl (e.g. aminoethyl; 2-(N,N-diethylamino)ethyl; 2-(4-morpholino) ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl;

cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleared by phosphotase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis

Compounds of the invention can be synthesised by a number of methods, examples of which are given below. Some synthesis routes are shown in Yamaguchi, et al., J. Med. Chem. 1993, 36, 4502–4068, which is herein incorporated by reference.

In general, a key step in the synthesis of these compounds is the addition/insertion of hydrazine, thus providing the adjacent nitrogen ring atoms in the central moiety. This addition of hydrazine is accomplished in particular by a ring insertion step in the routes exemplified below.

The formed aromatic ring (represented by -A-B—) is usually derivatised before the routes shown below, and starting materials with the desired structure and substituent pattern are either commercially available or readily synthesised. Route 2 exemplifies a strategy where the aromatic ring is already substituted at the beginning of the synthesis route.

The route illustrated leads to compounds where R$_N$ is H. The possible substituents at this position can be added by the use of an appropriate electrophile with suitable reaction conditions.

Further derivatisation of the groups on R$_C$ can be carried out using a variety of conventional methods, some of which are illustrated in 'Further derivatisation steps'.

Route 1

Part 1: Synthesis of 2-arylindan-1,3-diones

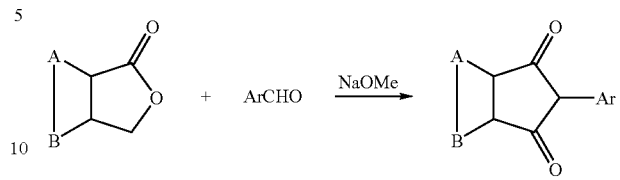

To an ice-cooled solution of phthalide or equivalent, (13.41 g; 0.1 mol) and the aromatic aldehyde (0.1 mol) in a mixture of methanol (50 ml) and ethylpropionate (50 ml) was added a solution of sodium methoxide in methanol [sodium (9.20 g; 0.4 mol) in methanol (50 ml)] with the temperature kept below 10° C. The solution was then heated to gentle reflux for 3 h, cooled to room temperature and poured onto water (500 ml). The mixture was washed with ether (5×100 ml) and the aqueous layer acidified with acetic acid and the solid filtered off. This was then used crude in the next stage.

Part 2: Reaction of 2-arylindan-1,3-ones with Hydrazine Hydrate

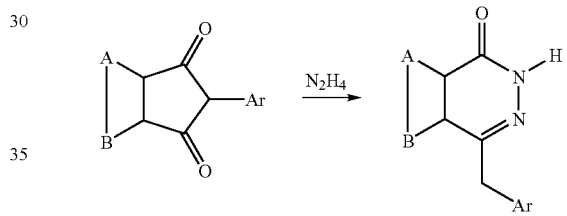

A suspension of 2-arylindan-1,3-dione (20 mmol) in hydrazine monohydrate (40 ml) was heated to reflux for 4 h, cooled and the product filtered off. The solid was washed with ethanol.

Route 2

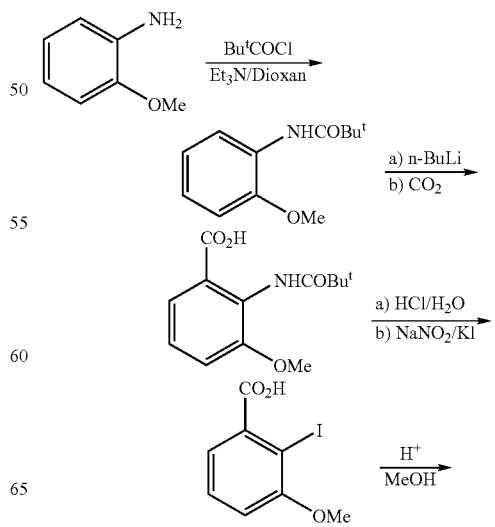

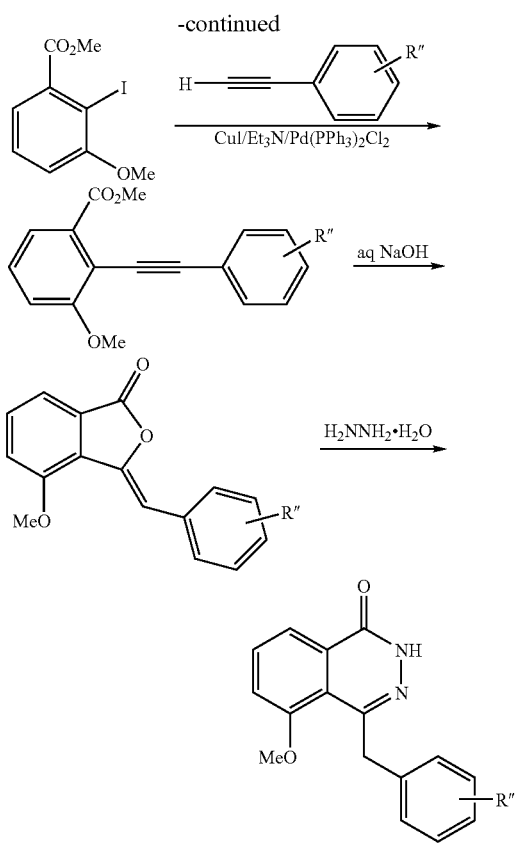

Pivaloyl chloride (120 g, 1 mol) was added dropwise at ambient temperature to a stirred solution of 2-methoxyaniline (123 g, 1 mol) and triethylamine (111 g, 1.1 mol) in 1,4-dioxane (1200 ml), the mixture was stirred at ambient temperature for 2 hours, then it was poured into water (3000 ml). The product was extracted into ethyl acetate (3×300 ml), then the combined extracts were dried (MgSO$_4$) and the solvents were removed in vacuo to give N-(2-methoxyphenyl)pivalamide (198 g; 96%) as a low-melting solid which was used without further purification.

n-Butyllithium (1.6M solution in hexane; 200 ml, 0.32 mol) was added dropwise under nitrogen at −10° C. to a stirred solution of N-(2-methoxyphenyl)pivalamide (27.6 g, 0.133 mol) in tetrahydrofuran (600 ml), the mixture was allowed to warm to ambient temperature, stirred for a further 2 hours, then it was added to a large excess of crushed solid carbon dioxide. The mixture was allowed to warm to ambient temperature, 3M hydrochloric acid (200 ml) was added and the tetrahydrofuran was removed in vacuo. The resulting solid was collected by filtration and crystallised from acetonitrile to give 3-methoxy-2-pivalamidobenzoic acid (21 g; 63%) as a solid, m.pt. 117–120° C. Concentration of the liquor yielded a second crop (2.6 g; 8%).

A stirred mixture of 3-methoxy-2-pivalamidobenzoic acid (20 g, 0.08 mol) and 7M hydrochloric acid (280 ml) was heated under reflux for 2 hours then cooled to 0° C. A solution of sodium nitrite (5.8 g, 0.09 mol) in water (46 ml) was added dropwise at <5° C., the mixture was stirred at 0–5° C. for 2 hours, then a solution of potassium iodide (17.8 g, 0.11 mol) in water (39 ml) was added dropwise at 0–5° C. The stirred mixture was heated at 70–80° C. for 2 hours then cooled in ice. The product was extracted into ethyl acetate (3×300 ml), the combined extracts were washed with 20% aqueous sodium thiosulphate solution (3×300 ml), then they were dried (MgSO$_4$) and the solvent was removed in vacuo to leave 2-iodo-3-methoxybenzoic acid (13 g, 58%) as a solid, m.pt. 142–146° C.

A stirred mixture of 2-iodo-3-methoxybenzoic acid (20 g, 0.07 mol; prepared in a manner similar to that described above), methanol (300 ml) and concentrated sulphuric acid (3.5 ml) was heated under reflux for 8 hours, cooled to ambient temperature and added to water (1500 ml). The product was extracted into dichloromethane (3×500 ml), the combined extracts were washed with 5% aqueous sodium hydroxide solution (3×500 ml), then they were dried (MgSO$_4$) and the solvent was removed in vacuo to give methyl 2-iodo-3-methoxybenzoate (18.5 g, 90%) as a solid, m.pt. 58–61° C.

The appropriately substituted phenylacetylene (0.063 mol) was added at ambient temperature under nitrogen to a stirred solution of copper(I) iodide (0.1 g, 6.3 mmol), bis(triphenylphosphine)palladium(II) dichloride (0.43 g, 6.3 mmol), and methyl 2-iodo-3-methoxybenzoate (18.5 g, 0.063 mol) in triethylamine (375 ml), the mixture was stirred at ambient temperature for 72 hours, then it was added to 5M hydrochloric acid (1000 ml). The product was extracted into ethyl acetate (3×400 ml), the combined extracts were dried (MgSO$_4$) and the solvent was removed in vacuo to give the methyl 3-methoxy-2-(substituted phenylethynyl)benzoate which was used without purification.

A mixture of the crude 3-methoxy-2-(substituted phenylethynyl)benzoate and 30% aqueous sodium hydroxide solution (302 ml) was stirred and heated under reflux for 4 hours, cooled to ambient temperature and acidified by the addition of concentrated sulphuric acid. The product was extracted into ether (3×500 ml), the combined extracts were washed with 10% aqueous sodium carbonate solution (2000 ml), then they were dried (MgSO$_4$) and the solvent was removed in vacuo to give 4-methoxy-3-(substituted benzylidene)phthalide which was used without purification.

A mixture of the crude 4-methoxy-3-(substituted benzylidene)phthalide (14 g) and hydrazine hydrate (83 ml) was heated under reflux for 5 hours then cooled to ambient temperature. The resulting solid was collected by filtration, washed well with ethanol and dried in vacuo to give the desired compound.

The substitution of the aromatic ring in the starting material can be altered as appropriate.

Route 3

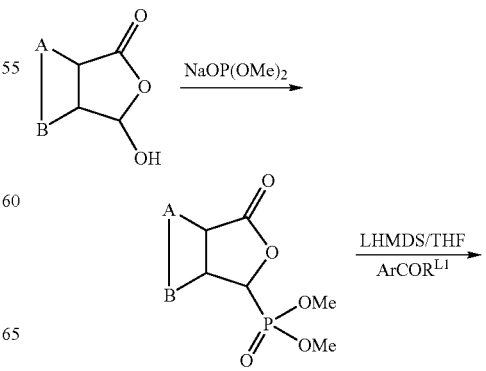

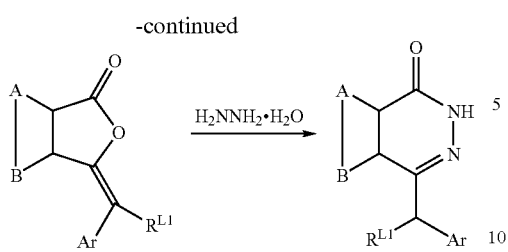

Dimethyl phosphite (11 g, 0.1 mol) then 2-formylbenzoic acid (10.51 g, 0.07 mol) or equivalent were added dropwise at 0° C. under nitrogen to a stirred solution of sodium methoxide [from sodium (2.3 g) in methanol (80 ml)], the mixture was stirred at ambient temperature for 30 minutes, then it was quenched by the addition of methanesulphonic acid (10.6 g, 0.11 mol). The methanol was removed in vacuo, the residue was partitioned between dichloromethane (200 ml) and water (50 ml), then the dichloromethane solution was washed with water (2×50 ml) and dried (MgSO$_4$). The solvent was removed in vacuo to leave dimethyl 3-oxobenzo[c]furan-1-ylphosphonate or equivalent.

Lithium hexamethyldisilazide (1M solution in hexanes; 33 ml, 0.033 mol) was added dropwise under nitrogen at −78° C. to a stirred solution of dimethyl 3-oxobenzo[c]furan-1-ylphosphonate (8 g, 0.033 mol) or equivalent in tetrahydrofuran (300 ml), then the mixture was stirred at −78° C. for 1 hour. The appropriate aryl alkyl ketone (0.03 mol) was added, the mixture was stirred at −78° C. for 1 hour, allowed to warm to 0° C., then it was quenched by the addition of an excess of saturated aqueous ammonium chloride solution. The aqueous phase was separated and shaken with dichloromethane (100 ml), then the combined organic solutions were dried (MgSO$_4$) and the solvents were removed in vacuo. The residue was triturated with hexane (50 ml) and the resulting solid was collected by filtration and air-dried to give 3-(α-alkylarylidene)phthalide or equivalent which was used without further purification.

A mixture of 3-(α-alkylarylidene)phthalide (0.019 mol) or equivalent and hydrazine hydrate (20 ml) was heated under reflux for 18 hours then cooled to 0° C. The resulting solid was collected by filtration, washed well with ethanol and air-dried to give the desired compound.

Further Derivatisation (a) Demethylation of 4-(methoxybenzyl)-1(2H)-phthalazinones

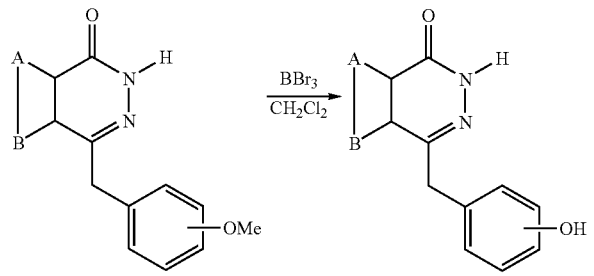

To a suspension of the methoxybenzylphthalazinone or equivalent (0.7 g; 2.65 mmol) in dichloromethane (5 ml) under nitrogen at room temperature was added a solution of boron tribromide in dichloromethane (1M; 6 ml; 6.0 mmol). The mixture was heated to reflux for 24 h, cooled and poured into sodium hydroxide (10%; 25 ml). The organic layer was removed and the aqueous layer acidified (HCl) and the solid filtered off.

(b) Derivatisation of 4-(aminobenzyl)-1(2H)-phthalazinones

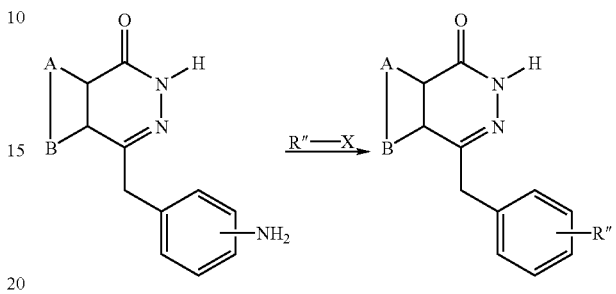

To a stirred solution of the aminobenzylphthalazinone or equivalent (0.6 g; 2.4 mmol) and triethylamine (0.24 g; 2.4 mmol) in 1,4-dioxan (50 ml) was added dropwise the electrophile (2.4 mmol). The mixture was then heated to reflux for 2 h, cooled and poured onto water (100 ml). The solid was then filtered of and washed with water and ethanol before drying in vacuo.

(c) Acylation of Hydroxybenzylphthalazinones

The acylation is generally carried out by the addition of the appropriate acid chloride to the hydroxybenzylphthalazinone under suitable conditions. Examples of this are given below:

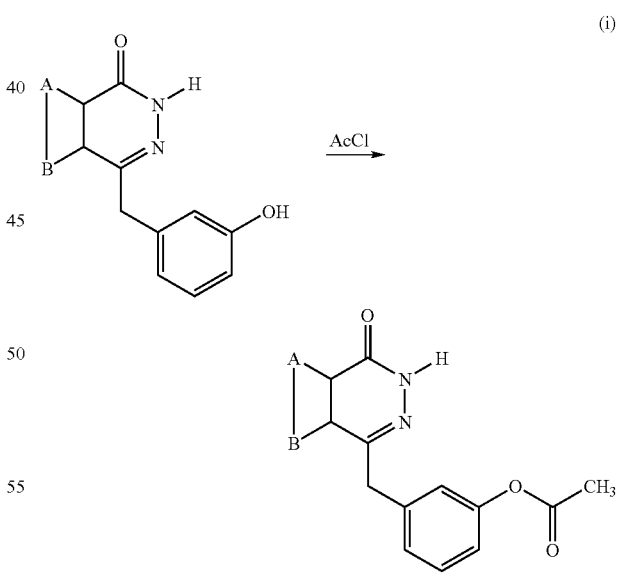

To a stirred solution of the hydroxybenzylphthalazinone or equivalent (e.g. 164) (0.7 g; 2.79 mmol) and triethylamine (0.28 g; 2.79 mmol) in 1,4-dioxan (40 ml) was added dropwise acetyl chloride (0.2 ml; 2.79 mmol). The mixture was then heated to reflux for 2 h, cooled and poured onto water (100 ml). The solid was then filtered of and washed with water and ethanol before drying in vacuo.

(ii)

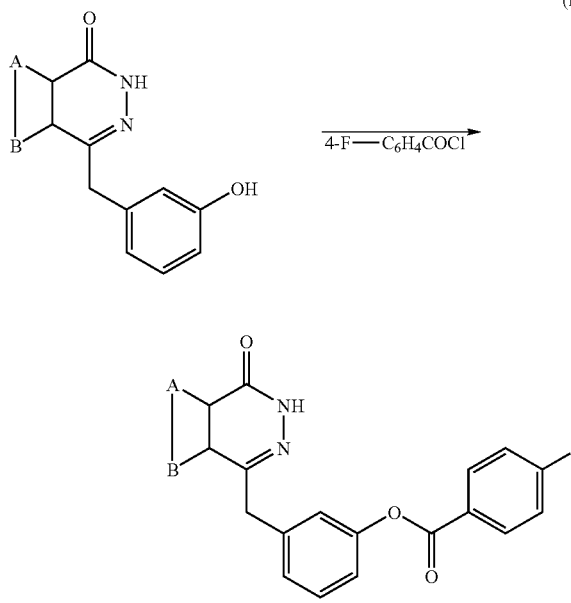

A stirred suspension of the hydroxybenzylphthalazinone (1.36 g; 5.41 mmol), triethylamine (0.61 g; 6.00 mmol) and 4-fluorobenzoyl chloride (0.86 g; 5.41 mmol) in dry 1,4-dioxan (50 ml) was heated under reflux, with the exclusion of moisture (CaCl$_2$), for 2 h and cooled to room temperature. The reaction mixture was then poured onto water (250 ml) and the solid filtered off. The crude solid was then boiled in cyclohexane (10 ml), cooled and filtered off.

(iii)

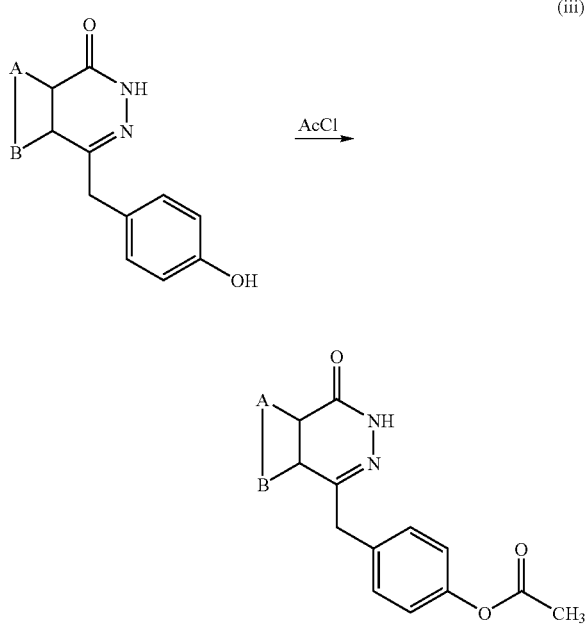

A stirred suspension of hydroxybenzylphthalazinone (0.70 g; 2.79 mmol) or equivalent, triethylamine (0.4 ml; 2.79 mmol) and acetylchloride (0.2 ml; 2.79 mmol) in dry 1,4-dioxan (40 ml) was heated to reflux, with the exclusion of moisture (CaCl$_2$), for 2 h and cooled to room temperature. The reaction mixture was then poured onto water (250 ml) and the solid filtered off.

(iv)

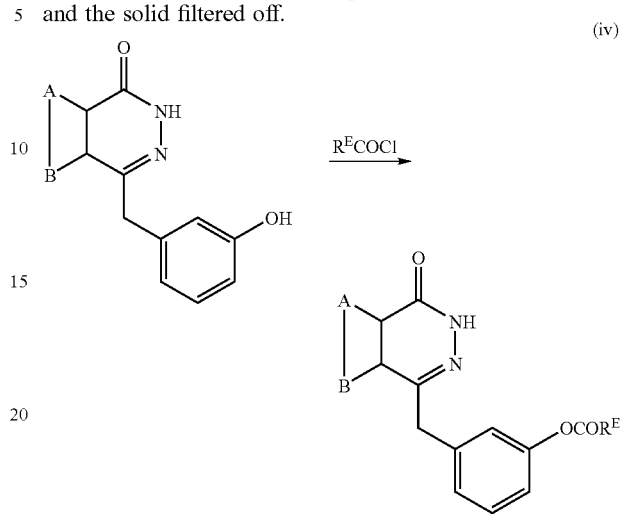

The appropriate acid chloride (0.24 mmol) was added to a stirred solution of 4-(3-hydroxybenzyl)phthalazin-1(2H)-one (50 mg, 0.2 mmol) or equivalent and triethylamine (33 μl) in 1,4-dioxane (0.5 ml) and the mixture was stirred at ambient temperature whilst the progress of the reaction was monitored by tlc. In some cases heating under reflux was necessary to force the reaction to proceed to completion. Once the reaction was complete, the mixture was diluted with ice-water and the product was extracted into ethyl acetate. The extract was washed with saturated aqueous sodium chloride solution and dried (MgSO$_4$), then the solvent was removed in vacuo. The residue was purified to give the required ester. The purification was carried out via preparative scale HPLC on a Gilson LC using a Jones Chromatography Genesis 4μ C18 column using gradient elution between aqueous trifluoroacetic acid and acetonitrile as eluents.

(d) Derivatisation of 3-(aminobenzyl)-1(2H)phthalazinones (i)

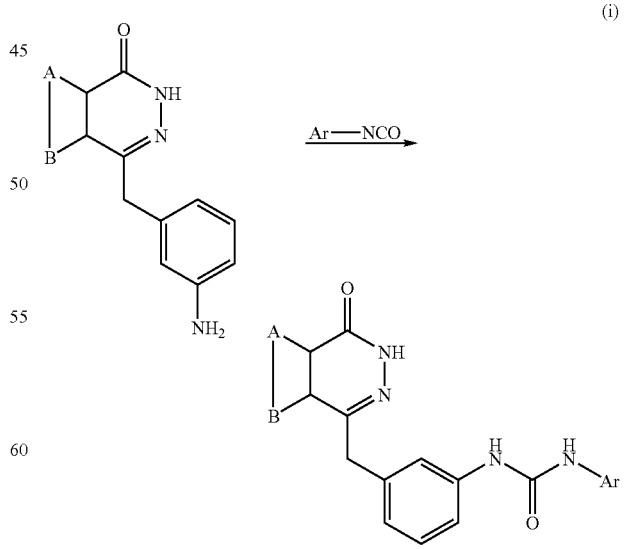

To a stirred solution of the aminobenzylphthalazinone (160) (1.00 g; 40 mmol) or equivalent in dry 1,4-dioxan (25 ml) at 40° C. was added the appropriate isocyanate (40 mmol). The mixture was stirred for a further 2 h, cooled to room temperature and the solid filtered off.

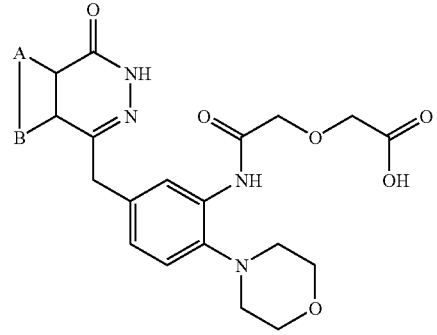

To a stirred solution of the aminophthalazinone (197) (1.00 g; 2.97 mmol) or equivalent in acetonitrile (25 ml) was added diglycolic anhydride (0.35 g; 3.00 mmol). The mixture was stirred at room temperature for 1 h, and the solid filtered off. The crude solid was dissolved in NaOH (10%; 20 ml) and filtered through Celite. The aqueous was then acidified and the solid filtered off.

(iii)

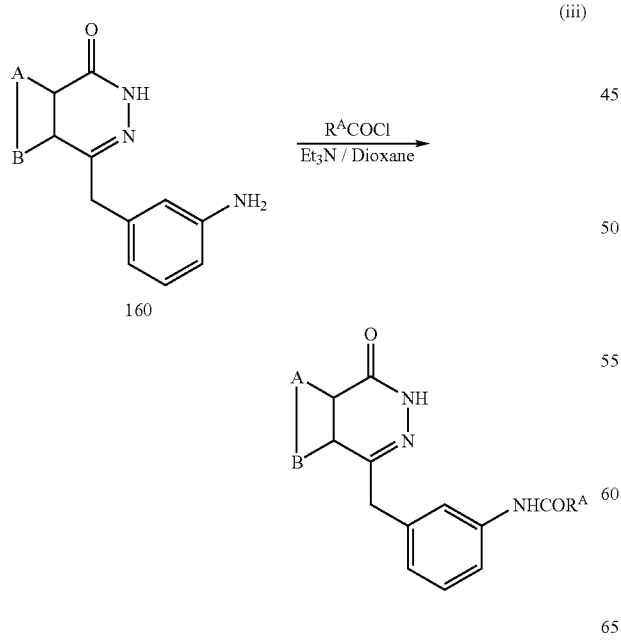

The appropriate acid chloride (0.2 mmol) was added to a stirred solution of the aminobenzylphthalazinone 160 (0.05 g, 0.2 mmol) or equivalent and triethylamine (33 μl) in 1,4-dioxane (0.5 ml), the mixture was stirred at ambient temperature for 18 hours, then it was diluted with water (10 ml). The product was collected by filtration, washed with water (5 ml) and dried in vacuo to give the required amide.

(iv)

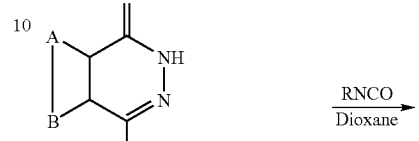

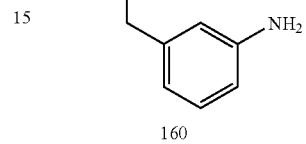

A mixture of the aminobenzylphthalazinone 160 (0.5 g, 2 mmol) or equivalent and 1,4-dioxane (15 ml) was stirred at ambient temperature until all of the solid had dissolved (5–15 minutes). The appropriate isocyanate (2 mmol) was added, the mixture was stirred at ambient temperature for 2 hours, then it was allowed to stand at ambient temperature for 18 hours. The resulting solid was collected by filtration, washed well with water and dried in vacuo to give the required ureido product.

(v) (a)

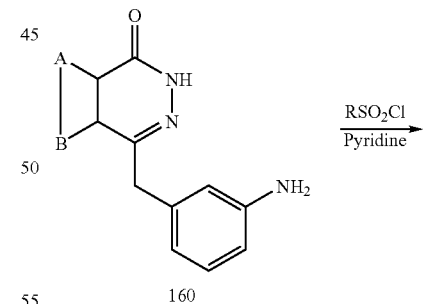

The appropriate sulphonyl chloride (1 mmol) was added to a solution of the aminobenzylphthalazinone 160 (0.25 g, 1 mmol) or equivalent in pyridine (10 ml), the stirred mixture was heated under reflux for 2 hours, then it was diluted with water (200 ml). The resulting solid was collected by filtration, washed well with water and dried in vacuo to give the required sulphonamido product.

(v) (b)

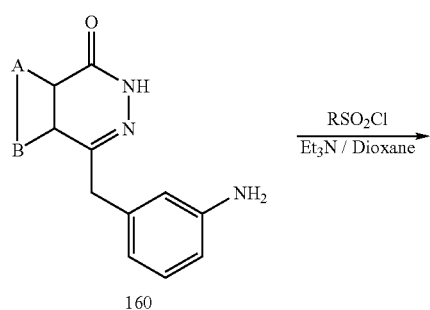

The appropriate sulphonyl chloride (1 mmol) was added to a solution of the aminobenzylphthalazinone 160 (0.25 g, 1 mmol) or equivalent and triethylamine (0.1 g, 1 mmol) in 1,4-dioxane (10 ml), the stirred mixture was heated under reflux for 2 hours, then it was diluted with water (200 ml). The resulting solid was collected by filtration, washed well with water and dried in vacuo to give the required sulphonamido product.

(e) Synthesis of 227

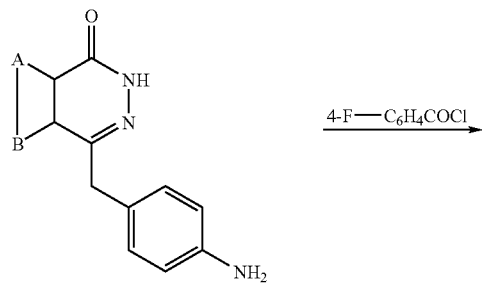

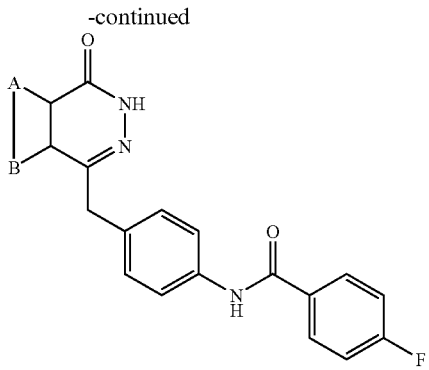

To a stirred solution of 4-fluorobenzoyl chloride (159) (0.95 g; 5.97 mmol) in dry 1,4-dioxan (50 ml) was added triethylamine (0.60 g; 5.97 mmol) and the aminobenzylphthalazinone (1.50 g; 5.97 mmol) or equivalent. The mixture was heated to reflux, with the exclusion of moisture (CaCl$_2$), for 2 h and cooled to room temperature. The reaction mixture was then poured onto water (250 ml) and the solid filtered off.

(f) Synthesis of 239

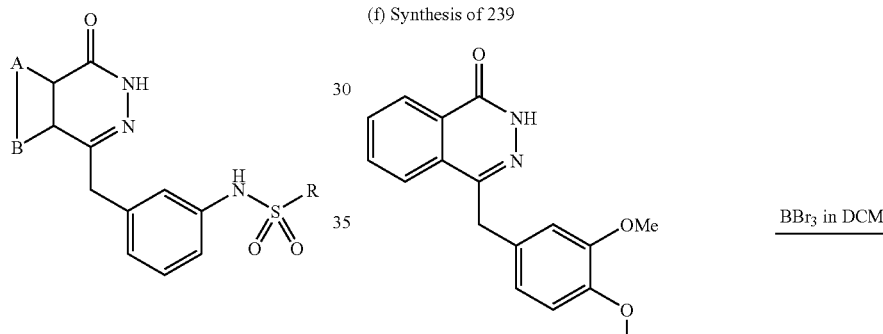

To a stirred suspension of the benzyloxymethoxy-benzylphthalazinone (187) (5.00 g; 13.0 mmol) in dichloromethane (11.5 ml) was added, under nitrogen, a solution of boron tribromide in dichloromethane (1.0 M solution; 4.4 ml; 4.40 mmol). The reaction mixture was then heated under reflux for 24 h, cooled to room temperature and poured into ice/water (250 ml). The mixture was then basified by the addition of solid sodium hydroxide and the organic layer removed. The aqueous layer was then washed with dichloromethane (3×50 ml) and acidified with concentrated HCl. The solid was filtered off, washed with water and air-dried.

(g) Synthesis of 247

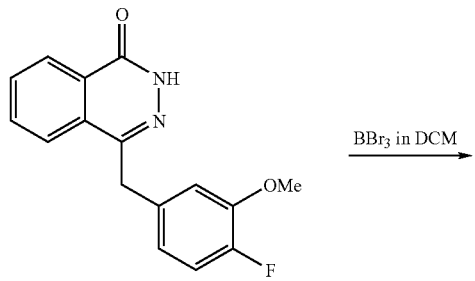

A stirred suspension of the starting methoxy-compound (241) (1.50 g; 5.27 mmol) in a solution of boron tribromide in dichloromethane (1.0 M solution; 12 ml; 12.00 mmol) was heated to reflux for 8 h under nitrogen. The reaction mixture was then cooled to room temperature and poured into ice/water (250 ml). The mixture was then basified by the addition of solid sodium hydroxide and the organic layer removed. The aqueous layer was then washed with dichloromethane (3×50 ml) and acidified with concentrated HCl. The solid was filtered off, washed with water and air-dried.

(h) Synthesis of 277

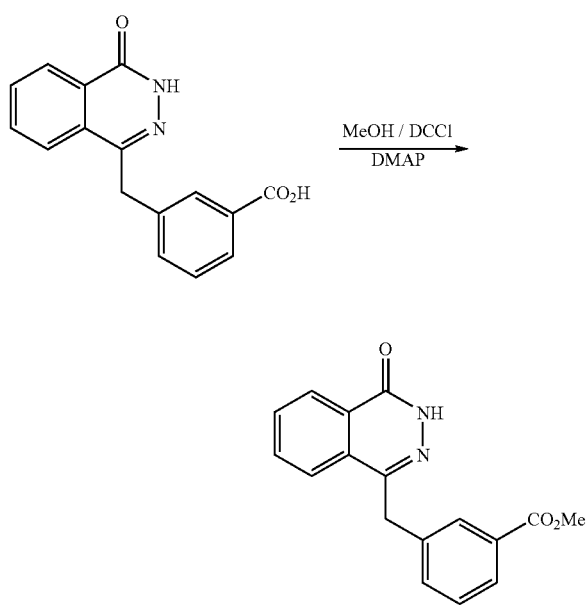

A solution of the carboxylic acid (276) (8 g, 0.028 mol) in dichloromethane (240 ml) was added dropwise at ambient temperature to a stirred mixture of dicyclohexylcarbodiimide (5.8 g, 0.028 mol), 4-(dimethylamino)pyridine (0.2 g, 0.0014 mol), methanol (0.92 g, 0.028 mol) and dichloromethane (40 ml), then the mixture was stirred at ambient temperature for 18 hours and filtered. The filter cake was washed with dichloromethane (280 ml), the filtrate and washings were combined and the solvent was removed in vacuo. The residue was diluted with ether (1000 ml), the resulting precipitate was removed by filtration, then the ethereal filtrate was washed with saturated aqueous sodium hydrogencarbonate solution (400 ml), 1.5M hydrochloric acid (400 ml), water (400 ml) and saturated aqueous sodium chloride solution (400 ml). The solution was dried (MgSO$_4$) and the solvent was removed in vacuo to give 277.

(i) Synthesis of 278

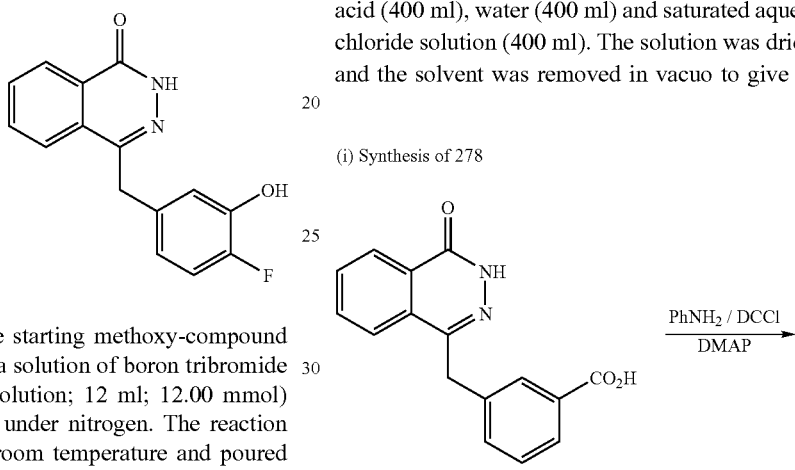

A solution of the carboxylic acid (276) (3 g, 0.01 mol) in dichloromethane (90 ml) was added dropwise at ambient temperature to a stirred mixture of dicyclohexylcarbodiimide (2.2 g, 0.01 mol), 4-(dimethylamino)pyridine (0.08 g, 0.5 mmol), aniline (0.9 g, 0.01 mol) and dichloromethane (15 ml), then the mixture was stirred at ambient temperature for 18 hours and filtered. The filter cake was washed with dichloromethane (105 ml), the filtrate and washings were combined and the solvent was removed in vacuo. The residue was diluted with ether (375 ml), the resulting precipitate was removed by filtration, then the ethereal filtrate was washed with saturated aqueous sodium hydrogencarbonate solution (150 ml), 1.5M hydrochloric acid (150 ml), water (150 ml) and saturated aqueous sodium chloride solution (150 ml). The solution was dried (MgSO$_4$) and the solvent was removed in vacuo to give 278.

(j) Derivitisation of 197

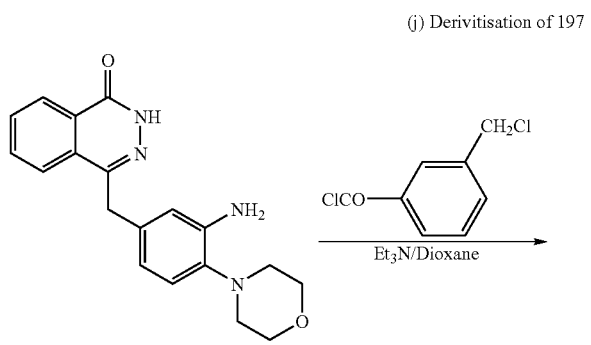

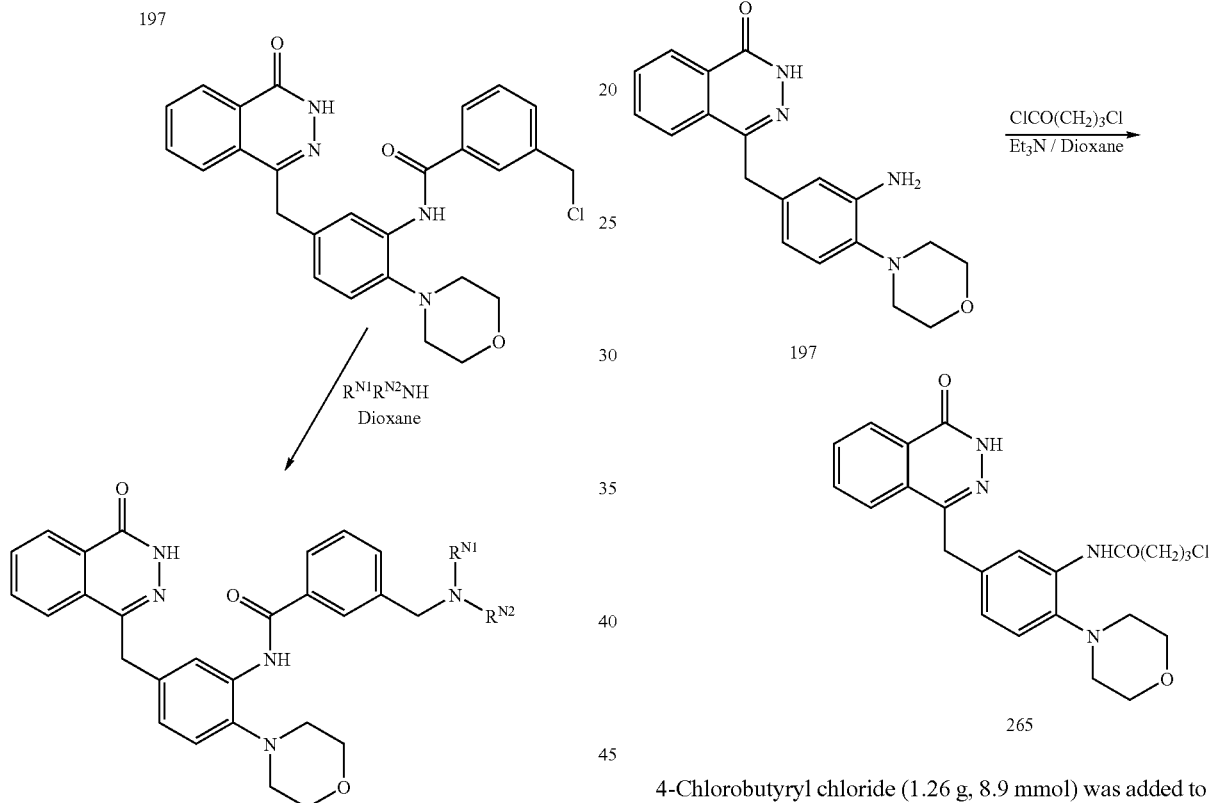

3-Chloromethylbenzoyl chloride (0.56 g, 3 mmol) was added to a stirred solution of 197 (1 g, 3 mmol) and triethylamine (0.4 ml) in 1,4-dioxane (50 ml), the mixture was stirred at ambient temperature for 2 hours, then it was diluted with water (100 ml). The product was extracted into ethyl acetate (3×50 ml), the combined extracts were dried (MgSO$_4$) and the solvent was removed in vacuo. The residue was triturated with hot toluene (50 ml), the hot solution was filtered (Celite), cyclohexane (50 ml) was added, and the mixture was allowed to cool to ambient temperature. The resulting solid was collected by filtration and dried in vacuo to give 3-(chloromethyl) -N-[2-morpholino-5-(1-oxophthalazin-4-ylmethyl)phenyl]benzamide (1.32 g, 90%) as a solid, m.pt. 117–122° C.

A mixture of 3-(chloromethyl)-N-[2-morpholino-5-(1-oxophthalazin-4-ylmethyl)phenyl]benzamide (0.66 g, 1.35 mmol), the appropriate amine(27 mmol) and 1,4-dioxane (50 ml) was heated under reflux for 2 hours, cooled to ambient temperature and diluted with water (100 ml) to precipitate a sticky solid. The aqueous layer was removed by decantation and the residual solid was extracted into ethyl acetate (3×50 ml). The combined extracts were washed with water (50 ml), dried (MgSO$_4$), then the solvent was removed in vacuo. The residue was triturated with hot toluene (50 ml), the hot solution was separated by decantation from insoluble material, cyclohexane (50 ml) was added, and the mixture was allowed to cool to ambient temperature. The resulting solid was collected by filtration, washed with cyclohexane (30 ml) and dried in vacuo to give the desired compound.

(k) Synthesis of 265

4-Chlorobutyryl chloride (1.26 g, 8.9 mmol) was added to a stirred solution of 197 (3 g, 8.9 mmol) and triethylamine (0.9 g, 8.9 mmol) in 1,4-dioxane (50 ml), the mixture was stirred at ambient temperature for 2 hours, then it was diluted with water (100 ml), causing a sticky semisolid to precipitate. The aqueous phase was removed by decantation, and the residue was triturated with hot ethyl acetate (100 ml). The hot solution was separated from an insoluble residue, and the solvent was removed in vacuo. The residue was triturated with cyclohexane (50 ml) and the resulting solid was collected by filtration and dried in vacuo to give 4-chloro-N-[2-morpholino-5-(1-oxophthalazin-4-ylmethyl)phenyl]butyramide.

Use

The present invention provides active compounds, specifically, active in inhibiting the activity of PARP.

The term "active," as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect," the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "adjunct" as used herein relates to the use of active compounds in conjunction with known therapeutic means. Such means include cytotoxic regimes of drugs and/or ionising radiation as used in the treatment of different cancer types.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

Active compounds may also be used as cell culture additives to inhibit PARP, for example, in order to radiosensitize cells to known chemo or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/ peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

Synthesis Data

The compounds of which the structures are shown in Table 1, with a number greater than 100 were synthesised according to the synthesised routes above—the characterisation data follows. The compounds in Table 1 with a number less than 100 are available from Maybridge plc, Cornwall, UK.

Route 1

(-A-B— benzene ring)

126; Ar4-chlorophenyl

Yield, 31%; mpt. 218–220° C.; $\delta_H$ 4.30 (2H, s), 7.30 (4H, s), 7.75–8.00 (3H, s), 8.25–8.45 (1H, m), 12.40 (1H, br s); m/z (M+H)$^{+\cdot}$ 271 (100%), 273 (35%).

129; Ar=4-bromophenyl

Yield, 59%; mpt. 232–235° C.; $\delta_H$ 4.40 (2H, s), 7.30 (2H, d, J=8.7 Hz), 7.45 (2H, d, J=8.7 Hz), 7.60–7.95 (3H, m), 8.25–8.45 (1H, m), 12.40 (1H, br s); m/z (M+H)$^{+\cdot}$ 314 (100%), 316 (95%).

131; Ar=1-naphthyl

Yield, 58%; mpt. 228–231° C.; $\delta_H$ 4.80 (2H, s), 7.25–8.50 (11H, m), 12.50 (1H, br s); m/z (M+H)$^{+\cdot}$ 287 (100%).

132; Ar=4-fluorophenyl

Yield, 54%; mpt. 194–197° C.; $\delta_H$ 4.30 (2H, s), 7.10 (2H, d, J=8.5 Hz), 7.25 (2H, d, J=8.5 Hz), 7.25–7.50 (1H, m), 7.75–8.00 (2H, m), 8.25–8.45 (1H, m), 12.55 (1H, br s); m/z (M+H)$^{+\cdot}$ 255 (100%).

138; Ar=4-methoxyphenyl

Yield, 66%; mpt. 194–196° C.; $\delta_H$ 3.70 (3H, s), 4.50 (2H, s), 6.85 (2H, d, J=8.5 Hz), 7.30 (2H, d, J=8.5 Hz), 7.70–8.00 (3H, m), 8.25–8.45 (1H, m), 12.50 (1H, br s); m/z (M+H)$^{+\cdot}$ 267 (100%).

139; Ar=4-methylphenyl

Yield, 80%; mpt. 205–207° C.; $\delta_H$ 2.15 (3H, s), 4.25 (2H, s), 7.00–7.30 (4H, m), 7.60–7.95 (3H, m,), 8.25–8.45 (1H, m), 12.60 (1H, br s); m/z (M+H)$^{+\cdot}$ 251 (100%).

141; Ar=2-fluorophenyl

Yield, 85%; mpt. 235–238° C.; $\delta_H$ 4.40 (2H, s), 7.10–7.45 (4H, m), 7.70–8.05 (3H, m), 8.25–8.45 (1H, m), 12.40 (1H, br s); m/z (M+H)$^{+\cdot}$ 255 (100%).

142; Ar =2-methoxyphenyl

Yield, 74%; mpt. 158–160° C.; $\delta_H$ 3.70 (3H, s), 4.25 (2H, s), 6.70–6.95 (3H, m), 7.10–7.35 (1H, m), 7.60–7.95 (3H, m), 8.45–8.55 (1H, m), 11.15 (1H, br s); m/z (M+H)$^{+\cdot}$ 281 (100%).

145; Ar=phenyl

Yield, 85%; mpt. 201–204° C.; $\delta_H$ 4.45 (2H, s), 7.20–7.45 (5H, m), 7.75–8.00 (3H, m), 8.25–8.45 (1H, m), 12.40 (1H, br s); m/z (M+H)$^{+\cdot}$ 237 (100%).

151; Ar=4-iodophenyl

Yield, 86%; mpt. 233–236° C.; $\delta_H$ 4.20 (2H, s), 7.15 (2H, d, J=8.2 Hz), 7.60 (2H, d, J=8.2 Hz), 7.75–7.95 (3H, m), 8.25–8.45 (1H, m), 12.15 (1H, br s); m/z (M+H)$^{+\cdot}$ 362 (100%).

159; Ar=4-aminophenyl

Yield, 28%; mpt. 233–236° C.; $\delta_H$ 4.15 (2H, s), 4.85 (2H, s), 6.50 (2H, d, J=7.1 Hz), 7.00 (2H, d, J=7.1 Hz), 7.75–7.95 (3H, m), 8.25–8.45 (1H, m), 12.50 (1H, br s); m/z (M+H)$^{+\cdot}$ 252 (100%).

160; Ar=3-aminophenyl

Yield, 95%; mpt. 178–180° C.; $\delta_H$ 4.15 (2H, s), 5.00 (2H, br s), 6.35–6.55 (3H, m), 6.80–7.05 (1H, m), 7.75–7.90 (3H, m), 8.25–8.40 (1H, m); m/z (M+H)$^{+\cdot}$ 252 (100%).

163; Ar=2-methylphenyl

Yield, 72%; mpt. 201–204° C.; $\delta_H$ 2.15 (3H, s), 4.10 (2H, s), 6.95–7.25 (4H, m), 7.80–7.95 (3H, m), 8.25–8.45 (1H, m), 12.25 (1H, br s).

177; Ar=4-pyridyl

Yield, 40%; mpt. 214–216° C.; $\delta_H$ 4.25 (2H, s), 7.45 (2H, d, J =5.7 Hz), 7.75–7.95 (3H, m), 8.25–8.45 (1H, m), 8.55 (2H, d, J=5.7 Hz), 12.00 (1H, br s); m/z (M+H)$^{+\cdot}$ 238 (100%).

178; Ar=3-pyridyl

Yield, 62%; mpt. 196–199° C.; $\delta_H$ 4.30 (2H, s), 7.25–7.45 (1H, m), 7.60–7.95 (4H, m), 8.25–8.45 (2H, m), 8.55 (1H, s), 12.15 (1H, br s); m/z (M+H)$^{+\cdot}$ 238 (100%).

180; Ar=3,4-methylenedioxyphenyl

Yield, 59%; mpt. 225–228° C.; $\delta_H$ 4.25 (2H, s), 6.00 (2H, s), 6.85–7.00 (3H, m), 7.70–7.95 (3H, m), 8.25–8.45 (1H, m), 12.25 (1H, br s); m/z (M+H)$^{+\cdot}$ 281 (100%).

186; Ar=3-chlorophenyl

Yield, 69%; mpt. 192–194° C.; $\delta_H$ 4.30 (2H, s), 7.30–7.50 (3H, s), 7.75–8.00 (3H, m), 8.25–8.45 (1H, m), 12.60 (1H, br s); m/z (M+H)$^{+\cdot}$ 271 (100%), 273 (35%).

187; Ar=3-benzyloxy-4-methoxyphenyl

Yield, 51%; mpt. 150–152° C.; $\delta_H$ 3.60 (3H, s), 4.20 (2H, s), 5.05 (2H, s), 7.30–7.50 (3H, s), 7.55 (5H, s), 7.75–8.00 (3H, m), 8.25–8.45 (1H, m), 12.50 (1H, br s); m/z (M–H)$^{+\cdot}$ 371(100%).

191; Ar=3-(trifluoromethyl)phenyl

Yield, 71%; mpt. 195–198° C.; $\delta_H$ 4.30 (2H, s), 7.50–8.00 (7H, m), 8.25–8.45 (1H, m), 11.60 (1H, br s); m/z (M+H)$^{+\cdot}$ 305 (100%).

192; Ar=3-fluorophenyl

Yield, 70%; mpt. 187–190° C.; $\delta_H$ 4.30 (2H, s), 6.90–7.45 (4H, m), 7.75–8.00 (3H, m), 8.25–8.45 (1H, m), 12.30 (1H, br s); m/z (M+H)$^{+\cdot}$ 255 (65%).

193; Ar=3-phenoxyphenyl

Yield, 52%; mpt. 146–148° C.; $\delta_H$ 4.20 (2H, s), 6.80–7.50 (9H, m), 7.75–8.00 (3H, m), 8.25–8.45 (1H, m), 12.00 (1H, br s); m/z (M+H)$^+$ 329 (45%).

194; Ar =3-benzyloxyphenyl

Yield, 83%; mpt 177–180° C.; $\delta_H$ 4.20 (2H, s), 5.00 (2H, s), 6.80–7.50 (9H, m), 7.75–8.00 (3H, m), 8.25–8.45 (1H, m), 12.00 (1H, br s).

198; Ar =3-amino-4-thiomorpholinophenyl

Yield, 6%; mpt. 235–238° C.; $\delta_H$ 2.75 (4H, br s), 2.95 (4H, br s), 4.10 (2H, s), 4.65 (2H, s), 6.50–6.85 (3H, m), 7.75–8.00 (3H, m), 8.25–8.45 (1H, m), 12.50 (1H, s); m/z (M+H)$^+$ 353 (100%).

202; Ar=3,4-difluorophenyl

Yield, 70%; mpt. 186–191° C.; $\delta_H$ 4.25 (2H, br s), 7.00–7.55 (3H, m), 7.75–8.00 (3H, m), 8.25–8.45 (1H, m), 12.50 (1H, s); m/z (M−H)$^+$ 271 (100%).

204; Ar=3-nitro-4-pyrrolidinophenyl

Yield, 1%; mpt. 268–270° C.; $\delta_H$ 2.75 (4H, br s), 3.10 (4H, br s), 4.10 (2H, s), 6.85 (1H, d, J=8.15 Hz), 7.45 (1H, dd, J=<2 Hz and 8.15 Hz), 7.75–8.00 (3H, m), 8.25–8.45 (1H, m), 12.50 (1H, s); m/z (M+H)$^+$ 351 (100%).

211; Ar=3-bromophenyl

Yield, 80%; mpt 199–202° C.; $\delta_H$ 4.35 (2H, s), 7.20–7.60 (4H, m), 7.75–8.00 (3H, m), 8.25–8.45 (1H, m), 12.40 (1H, s); m/z (M+H)$^+$ 316 (95%) and 318 (100%).

222; Ar=4-benzyloxy-3-methoxyphenyl

Yield, 29%; mpt. 173–175° C.; $\delta_H$ 3.60 (3H, s), 4.10 (2H, s), 5.00 (2H, s), 6.60–6.95 (3H, m), 7.40 (5H, s), 7.75–8.00 (3H, m), 8.25–8.45 (1H, m), 12.50 (1H, s); m/z (M+H)$^+$ 373 (100%).

241; Ar=4-fluoro-3-methoxyphenyl

Yield, 55%; mpt. 211–214° C.; $\delta_H$ 3.80 (3H, s), 4.25 (2H, s), 6.75–7.25 (3H, m), 7.75–8.00 (3H, m), 8.25–8.45 (1H, m), 12.50 (1H, s); m/z (M+H)$^+$ 285 (100%).

248; Ar=2-fluorophenyl

Yield, 86%; mpt. 234–236° C.; $\delta_H$ 4.30 (2H, s), 4.65 (2H, s), 7.00–7.45 (4H, m), 7.75–8.00 (3H, m), 8.25–8.45 (1H, m), 12.50 (1H, s); m/z (M+H)$^+$ 255 (100%).

249; Ar=2-pyridyl

Yield, 84%; mpt. 180–184° C.; $\delta_H$ 4.45 (2H, s), 7.10–7.45 (2H, m), 7.50–8.00 (4H, m), 8.25–8.45 (1H, m), 8.45–8.55 (1H, m), 12.50 (1H, s); m/z (M+H)$^+$ 238 (100%).

266; Ar=2-phenylethyl

Yield, 9%; m.pt. 124–126° C.; m/z (M)$^+$ 250 (70% purity).

276; Ar=3-carboxyphenyl

Yield, 59%; m.pt. 277–280° C.; $\delta_H$ 4.40 (2H, s), 7.3–8.0 (7H, m), 8.1–8.4 (1H, m) and 12.60 (1H, s); m/z (M+H)$^+$ 281 (88% purity).

Route 2

279; R″=4-methyl

Yield, 5% over 7 stages; m.pt. 215–217° C.; $\delta_H$ 2.20 (3H, s), 3.80 (3H, s), 4.40 (2H, s), 7.10 (4H, s), 7.40 (1H, dd), 7.70–7.90 (2H, m) and 12.60 (1H, br s); m/z (M+H)$^+$ 281 (100% purity).

Route 3

(-A-B— =benzene ring)

Intermediate compound: dimethyl 3-oxobenzo[c]furan-1-ylphosphonate Yield, 90%; m.pt. 95–96.5° C.

283; Ar=phenyl, R$^{L1}$=propyl

Yield, 49% over 2 stages; m.pt. 158–159° C.; $\delta_H$ 0.90 (3H, t), 1.0–1.5 (2H, m), 1.8–2.5 (2H, m), 4.40 (1H, t), 7.1–7.4 (5H, m), 7.5–7.9 (3H, m), 8.4–8.6 (1H, m) and 12.0 (1H, br s); m/z (M+H)$^+$ 279 (98% purity).

284 (found to be a 7:1 mixture of pairs of diastereoisomers); ArCOR$^{L1}$=2-methylindanone Yield, 46% over 2 stages; m.pt. 204–206° C.; $\delta_H$ 0.70 and 1.10 (3H, 2×d), 2.5–3.4 (3H, m), 4.50 and 5.1 (1H, 2×d), 6.8–7.3 (4H, m), 7.95 (3H, s), 8.3–8.5 (1H, m) and 12.5 (1H, br s); m/z (M+H)$^+$ 277 (100% purity over 2 pairs of diastereoisomers).

285; Ar=phenyl, R$^{L1}$=methyl

Yield, 50% over 2 stages; m.pt. 169–171° C.; $\delta_H$ 1.60 (3H, d), 4.80 (1H, q), 7.1–7.4 (5H, m), 7.7–7.9 (3H, m), 8.25–8.4 (1H. m) and 12.7 (1H, br s); m/z (M+H)$^+$ 251 (100% purity).

Further Derivatisation (a)

164; 4-hydroxy

Yield, 99%; mpt. 231–234° C.; $\delta_H$ 4.15 (2H, s), 6.60 (2H, d, J=8.0 Hz), 7.10 (2H, d, J=8.0 Hz), 7.80–7.95 (3H, m), 8.25–8.45 (1H, m), 12.50 (1H, s); m/z (M+H)$^+$ 253 (100%).

165; 3-hydroxy

Yield, 68%; mpt. 198–201° C.; $\delta_H$ 4.15 (2H, s), 6.50–6.80 (3H, m,), 6.95–7.10 (1H, m), 7.80–7.95 (3H, m), 8.25–8.45 (1H, m), 12.50 (1H, s); m/z (M+H)$^+$ 253 (100%). (b)

166; R″=4-NHC(=O)CH$_3$

Yield, 57%; mpt. 267–271° C.; $\delta_H$ 2.00 (3H, s), 4.25 (2H, s), 7.25 (2H, d, J=7.7 Hz), 7.55 (2H, d, J=7.7 Hz), 7.75–7.95 (3H, m), 8.25–8.45 (1H, m), 9.80 (1H, s), 12.50 (1H, br s); m/z (M+H)$^+$ 294 (100%).

167; R″4-NHC(=O)Ph

Yield, 87%; mpt. 293–296° C.; $\delta_H$ 4.25 (2H, s), 7.20–8.00 (12H, m), 8.25–8.45 (1H, m), 10.15 (1H, s), 12.50 (1H, s); m/z (M+H)$^+$ 356 (100%).

169; R″=3-NHC(=O)-2-thienyl

Yield, 72%; mpt. 232–235° C.; $\delta_H$ 4.25 (2H, s), 7.00–7.45 (3H, m), 7.55–7.65 (2H, m), 7.75–7.95 (5H, m), 8.25–8.45 (1H, m), 10.10 (1H, s), 12.50 (1H, br s); m/z (M+H)$^+$ 362 (100%).

170; R″=3-NHC(=O)-4-fluorophenyl

Yield, 68%; mpt. 257–261° C.; $\delta_H$ 4.25 (2H, s), 7.00–7.50 (4H, m), 7.55–8.25 (8H, m), 10.15 (1H, s), 12.50 (1H, br s); m/z (M+H)$^+$ 374 (100%).

171; R″=3-NHC(=O)Ph

Yield, 78%; mpt. 261–264° C.; $\delta_H$ 4.25 (2H, s), 7.05–7.95 (12H, m), 10.05 (1H, s), 12.50 (1H, s); m/z (M+H)$^+$ 356 (100%).

172; R″=3-NHC(=O)CH$_3$

Yield, 55%; mpt. 270–272° C.; $\delta_H$ 2.00 (3H, s), 4.25 (2H, s), 7.00–7.50 (4H, m), 7.75 (3H, s), 8.25–8.45 (1H, m), 9.80 (1H, s), 12.50 (1H, br s); m/z (M+H)$^+$ 294 (100%).

233; R″=3-NHC(=O)CH(Et)Ph

Yield, 82%; m.pt. 150–154° C.; $\delta_H$ 0.90 (3H, t), 1.50–2.25 (2H, m), 3.20–3.55 (1H, m), 4.25 (2H, s), 7.0–7.90 (12H, m), 8.25–8.45 (1H, m), 9.95 (1H, br s) and 12.50 (1H, br s); m/z (M+H)$^+$ 398 (88% purity).

(c) (i)

179; Yield, 45%; mpt. 161–164° C.; $\delta_H$ 2.15 (3H, s), 4.25 (2H, s), 6.90–7.35 (4H, m), 7.75–7.95 (3H, m), 8.25–8.45 (1H, m), 12.50 (1H, br s); m/z (M+H)$^+$ 295 (100%).

(c)(ii)

212; Yield, 55%; mpt. 184–187° C.; $\delta_H$ 3.55 (2H, s), 7.10–7.50 (6H, m), 7.75–8.05 (3H, m), 8.10–8.45 (3H, m), 12.55 (1H, s).

(c)(iii)

213; Yield, 12%; mpt 193–196° C.; $\delta_H$ 2.20 (3H, s), 3.55 (2H, s), 7.10 (4H, dd, J=8.2 Hz), 7.75–8.00 (3H, m), 8.25–8.45 (1H, m), 12.55 (1H, s).

(c)(iv)

289; $R^E$=n-C$_9$H$_{19}$; m/z (M+H)$^+$ 407 (purity >95%)
290; $R^E$=1-phenylsulphonylindol-3-yl
291; $R^E$=4-(N,N-dipropylsulphamoyl)phenyl; m/z (M+H)$^+$ 520 (purity >95%)
292; $R^E$=2-(4-methoxyphenoxy)-5-nitrophenyl; m/z (M+H)$^+$ 524 (purity >95%)
293; $R^E$=4-(4-chlorophenylsulphonyl)-3-methyl-2-thienyl; m/z (M+H)$^+$ 551 (purity >95%)
294; $R^E$=5-(2,3-dihydrobenzo[b]furan-5-yl)-4-methylthiazol-5-yl; m/z (M+H)$^+$ 496 (purity >95%)
295; $R^E$=2-(2-thienyl)thiazol-4-yl; m/z (M+H)$^+$ 446 (purity >95%)
296; $R^E$=3-methyl-5-(5-methylisoxazol-3-yl)isoxazol-4-yl; m/z (M+H)$^+$ 443 (purity >95%)
298; $R^E$=5-(4-chlorophenyl)-2-(trifluoromethyl)-3-furyl; m/z (M+H)$^+$ 525 (purity >95%)
299; $R^E$=2-(4-methylphenylthio)-3-pyridyl   300; $R^E$=quinoxalin-6-yl; m/z (M+H)$^+$ 409 (purity >85%)
601; $R^E$=2-chloro-3,4-dimethoxystyryl; m/z (M+H)$^+$ 477 (purity >90%)
602; $R^E$=5-phenyloxazol-4-yl; m/z (M+H)$^+$ 424 (purity >85%)
603; $R^E$=1-benzyloxycarbonylpiperid-4-yl; m/z (M+H)$^+$ 498 (purity >95%)
604; $R^E$=1-(4-methoxyphenyl)-5-methylpyrazol-4-yl; m/z (M+H)$^+$ 467 (purity >95%)
605; $R^E$=4-n-hexylphenyl; m/z (M+H)$^+$ 441 (purity >95%)
607; $R^E$=4-n-propylphenyl; m/z (M+H)$^+$ 399 (purity >95%)
608; $R^E$=6-fluoro-1,3-benzodioxan-8-yl; m/z (M+H)$^+$ 433 purity >95%)
609; $R^E$=2,4,5-trifluoro-3-methoxyphenyl; m/z (M+H)$^+$ 441 (purity >95%)
610; $R^E$=cyclohexyl; m/z (M+H)$^+$ 363 (purity >95%)
611; $R^E$=4-bromo-1-ethyl-3-methylpyrazol-5-yl
612; $R^E$=2-chloro-4-pyridyl; m/z (M+H)$^+$ 392/394 (purity >95%)
613; $R^E$=cyclopropyl; m/z (M+H)$^+$ 321 (purity >95%)
614; $R^E$=5-methyl-2-(trifluoromethyl)-3-furyl; m/z (M+H)$^+$ 429 (purity >95%)
615; $R^E$=cyclobutyl; m/z (M+H)$^+$ 335 (purity >95%)
616; $R^E$=2-chloro-6-methyl-4-pyridyl
617; $R^E$=1-(4-chlorophenoxy)-1-methylethyl; m/z (M+H)$^+$ 446/451 (purity >95%)
618; $R^E$=2-thienyl; m/z (M+H)$^+$ 363 (purity >90%)
619; $R^E$=3,4-methylenedioxyphenyl; m/z (M+H)$^+$ 401 (purity >95%)
620; $R^E$=n-heptyl; m/z (M+H)$^+$ 379 (purity >95%)
621; $R^E$=3-chloropropyl; m/z (M+H)$^+$ 357/359 (purity >95%)
622; $R^E$=5-methylisoxazol-3-yl; m/z (M+H)$^+$ 362 (purity >95%)
623; $R^E$=1-t-butyl-5-methylpyrazol-3-yl; m/z (M+H)$^+$ 417 (purity >90%)
624; $R^E$=3-phenylthiazol-4-yl; m/z (M+H)$^+$ 440 (purity >95%)
625; $R^E$=3-t-butyl-1-(2,4-dichlorobenzyl)pyrazol-5-yl
626; $R^E$=1-chloroethyl
627; $R^E$=3,4-dihydro-2H-1,5-benzodioxepin-7-yl
628; $R^E$=1-ethylpentyl; m/z (M+H)$^+$ 379 (purity >90%)
629; $R^E$=1-benzyloxycarbonyl-2,3-diydroindol-2-yl; m/z (M+H)$^+$ 532 (purity >90%)
630; $R^E$=2-chloro-1,1-dimethylethyl; m/z (M+H)$^+$ 371/373 (purity >95%)
631; $R^E$=1-propenyl; m/z (M+H)$^+$ 321 (purity >95%)
(d)(i)
215; Ar=phenyl
Yield, 31%; mpt. 254–257° C.; $\delta_H$ 3.55 (2H, s), 6.80–7.50 (13H, m), 7.85 (1H, s), 9.55 (1H, s); m/z (M+H)$^+$ 371 (100%).
216; Ar=4-fluorophenyl
Yield, 79%; mpt. 240–244° C.; $\delta_H$ 3.55 (2H, s), 6.80–7.50 (12H, m), 8.50 (1H, s), 9.55 (1H, s); m/z (M+H)$^+$ 389 (100%).
(d)(ii)
206; Yield, 12%; mpt. 125–126.5° C.; $\delta_H$ 2.65 (4H, br s), 3.70 (4H, br s), 4.20 (2H, s), 4.30 (4H, s), 7.00–7.15 (2H, m), 7.65–8.00 (3H, m), 8.25–8.45 (2H, m), 9.60 (1H, s), 12.55 (1H, s).
(d)(iii)
640; $R^4$=cyclobutyl
Yield, 77%; m/z (M+H)$^+$ 334 (96% purity).
641; $R^4$=5-methyl-2-(trifluoromethyl)-3-furyl
Yield, 50%; m/z (M+H)$^+$ 428 (97% purity).
642; $R^4$=4-bromo-1-ethyl-3-methylpyrazol-5-yl
Yield, 97%; m/z (M+H)$^+$ 466/468 (100% purity).
643; $R^4$=2-thienyl
Yield, 100%; m/z (M+H)$^+$ 362 (93% purity).
644; $R^4$=5-methylisoxazol-3-yl
Yield, 99%; m/z (M+H)$^+$ 361 (100% purity).
645; $R^4$=3,4-methylenedioxyphenyl
Yield, 100%; m/z (M+H)$^+$ 400 (94% purity).
646; $R^4$=1-t-butyl-5-methylpyrazol-3-yl
Yield, 96%; m/z (M+H)$^+$ 416 (97% purity).
647; $R^4$=1-ethylpentyl
Yield, 80%; m/z (M+H)$^+$ 378 (100% purity).
648; $R^4$=n-heptyl
Yield, 76%; m/z (M+H)$^+$ 378 (100% purity).
649; $R^4$=1-chloroethyl
Yield, 65%; m/z (M+H)$^+$ 342/344 (100% purity).
650; $R^4$=1-propenyl
Yield, 91%; m/z (M+H)$^+$ 320 (97% purity).
651; $R^4$=3,4-dihydro-2H-1,5-benzodioxepin-7-yl
Yield, 93%; m/z (M+H)$^+$ 428 (97% purity).
652; $R^4$=2-chloro-6-methyl-4-pyridyl
Yield, 77%; m/z (M+H)$^+$ 405/407 (100% purity).
653; $R^4$=2-chloro-4-pyridyl
Yield, 87%; m/z (M+H)$^+$ 391/393 (100% purity).
654; $R^4$=1-(4-chlorophenoxy)-1-methylethyl
Yield, 89%; m/z (M+H)$^+$ 448/450 (100% purity).
655; $R^4$=4-(trifluoromethoxy)phenyl
Yield, 100%; m/z (M+H)$^+$ 440 (100% purity).
656; $R^4$=cyclohexyl
Yield, 75%; m/z (M+H)$^+$ 362 (97% purity).
657; $R^4$=6-fluoro-1,3-benzodioxan-8-yl
Yield, 87%; m/z (M+H)$^+$ 432 (97% purity).
658; $R^4$=4-propylphenyl
Yield, 79%; m/z (M+H)$^+$ 398 (100% purity).
659; $R^4$=2,4,5-trifluoro-3-methoxyphenyl
Yield, 83%; m/z (M+H)$^+$ 440 (100% purity).
667; $R^4$=2-chloro-3,4-dimethoxystyryl
Yield, 76%; m/z (M+H)$^+$ 476/478 (100% purity).
668; $R^4$=4-hexylphenyl
Yield, 63%; m/z (M+H)$^+$ 440 (100% purity).
669; $R^4$=2-(4-methylphenoxy)-3-pyridyl
Yield, 41%; m/z (M+H)$^+$ 463 (97% purity).
670; $R^4$=2-(4-methylphenylthio)-3-pyridyl
Yield, 100%; m/z (M+H)$^+$ 479 (88% purity).
671; $R^4$=quinoxalin-6-yl
Yield, 86%; m/z (M+H)$^+$ 408 (100% purity).
672; $R^4$=1-benzyloxycarbonylpiperid-4-yl
Yield, 84%; m/z (M+H)$^+$ 497 (95% purity).
673; $R^4$=1-(4-methoxyphenyl)-5-methylpyrazol-4-yl
Yield, 76%; m/z (M+H)$^+$ 466 (97% purity).
674; $R^4$=5-(2-pyridyl)-2-thienyl
Yield, 66%; m/z (M+H)$^+$ 439 (100% purity).

675; $R^4$=5-phen yloxazol-4-yl

Yield, 63%; m/z (M+H)$^+$ 423 (100% purity).

676; $R^4$=3-methyl-5-(5-methylisoxazol-3-yl) isoxazol-4-yl

Yield, 49%; m/z (M+H)$^+$ 442 (100% purity).

677; $R^4$=2 (2-thienyl)isothiazol-4-yl

Yield, 70%; m/z (M+H)$^+$ 445 (100% purity).

678; $R^4$=2-(2,3-dihydrobenzo[b]furan-5-yl)-4-methylthiazol-5-yl

Yield, 96%; m/z (M+H)$^+$ 495 (100% purity).

679; $R^4$=5-(4-chlorophenyl)-2-(trifluoromethyl)-3-furyl

Yield, 95%; m/z (M+H)$^+$ 524/526 (98% purity).

680; $R^4$=3,5-bis-(trifluoromethyl)phenyl

Yield, 69%; m/z (M+H)$^+$ 492 (100% purity).

681; $R^4$=4-(4-chlorophenylsulphonyl)-3-methyl-2-thienyl

Yield, 45%; m/z (M+H)$^+$ 550/552 (100% purity).

682; $R^4$=1-benzyl-3-t-butylpyrazol-5-yl

Yield, 94%; m/z (M+H)$^+$ 492 (98% purity).

683; $R^4$=1-phenylsulphonylindol-3-yl

Yield, 90%; m/z (M+H)$^+$ 535 (100% purity).

684; $R^4$=n-nonyl

Yield, 75%; m/z (M+H)$^+$ 406 (94% purity).

685; $R^4$=2-(4-methoxyphenoxy)-5-nitrophenyl

Yield, 98%; m/z (M+H)$^+$ 523 (100% purity).

686; $R^4$=propyl

Yield, 56%; m/z (M+H)$^+$ 322 (92% purity).

687; $R^4$=ethyl

Yield, 68%; m/z (M+H)$^+$ 308 (97% purity).

688; $R^4$=1-methylethyl

Yield, 100%; m/z (M+H)$^+$ 322 (100% purity).

(d) (iv)

691; R=6-fluoro-1,3-benzodioxan-8-yl

Yield, 100%; m.pt. 250–254° C. (shrinks 142–146° C.); m/z (M+H)$^+$ 447 (100% purity).

692; R=3,4-dihydro-2H-1,5-benzodioxepin-7-yl

Yield, 71%; m.pt. 205–208° C.; m/z (M+H)$^+$ 443 (100% purity).

693; R=1-benzyloxycarbonylpiperid-4-yl

Yield, 78%; m.pt. 216–219° C.; m/z (M+H)$^+$ 512 (100% purity).

694; R=propyl

Yield, 75%; m.pt. 205–208° C.; $\delta_H$ 0.80 (3H, t), 1.2–1.7 (2H, m), 3.0 (2H, q), 4.20 (2H, s), 6.0 (1H, br s), 6.8–7.3 (4H, m), 7.7–7.95 (3H, m), 8.3–8.45 (2H, m) and 12.55 (1H, s); m/z (M+H)$^+$ 337 (100% purity).

698; R=2,3-dihydrobenzo[b]furan-5-yl

Yield, 88%; m.pt. 251–254° C.; $\delta_H$ 3.1 (2H, t), 4.25 (2H, s), 4.5 (2H, t), 6,6 (1H, d), 6.8–6.4 (6H, m), 7.7–7.9 (3H, m), 8.2–8.4 (2H, m), 9.0 (1H, s) and 12.55 (1H, s); m/z (M+H)$^+$ 413 (94% purity).

699; R=3-methoxyphenyl

Yield, 67%; m.pt. 195–200° C.; $\delta_H$ 3.7 (3H, s), 4.25 (2H, s), 6.4–6.6 (1H, m), 6.8–7.3 (7H, m), 9.7–9.9 (3H, m), 8.2–8.4 (1H, m), 8.6–8.7 (2H, m) and 12.25 (1H, s); m/z (M+H)$^+$ 401 (100% purity).

700; R=2-(trifluoromethoxy)phenyl

Yield, 84%; m.pt. 229–231° C.; $\delta_H$ 4.25 (2H, s), 6.9–7.3 (7H, m), 9.7–9.9 (3H, m), 8.2–8.4 (3H, m) 11.25 (1H, s) and 12.25 (1H, s); m/z (M+H)$^+$ 455 (100% purity).

701; R=5-methyl-3-phenylisoxazol-4-yl

Yield, 39%; m.pt. 256–258° C.; m/z (M+H)$^+$ 452 (97% purity).

704; R=2-ethoxyphenyl

Yield, 77%; m.pt. 174–178° C.; m/z (M+H)$^+$ 415 (100% purity).

705; R=4-butylphenyl

Yield, 78%; m.pt. 201–205° C.; $\delta_H$ 0.80 (3H, t), 1.0–1.8 (4H, m), 2.5 (2H, m), 4.25 (2H, s), 6.9–7.4 (8H, m), 9.7–9.9 (3H, m), 8.2–8.6 (3H, m) and 12.25 (1H, s); m/z (M+H)$^+$ 427 (100% purity).

706; R=butyl

Yield, 65%; m.pt. 225–227° C.; m/z (M+H)$^+$ 351 (96% purity).

(d)(v)(a)

697; R=methyl

Yield, 78%; m.pt. 192–194° C.; m/z (M+H)$^+$ 330 (100% purity).

(d)(v)(b)

702; R=4-acetamidophenyl

Yield, 67%; m.pt. 263–265° C.; m/z (M+H)$^+$ 449 (97% purity).

703; R =5-(2-pyridyl)-2-thienyl

Yield, 80%; m.pt. 258–261° C.; m/z (M+H)$^+$ 475 (100% purity).

(e)

227; Yield, 31%; mpt. 124–125.5° C.; $\delta_H$ 4.25 (2H, s), 7.20–7.50 (4H, m), 7.60–8.45 (8H, m), 10.20 (1H, m), 12.55 (1H, m); m/z (M–H)$^+$ 372 (20%).

(f)

239; Yield, 68%; mpt. 230–232° C.; $\delta_H$ 3.65 (2H, s), 4.10 (3H, s), 6.50–7.00 (3H, m), 7.75–8.00 (3H, m), 8.25–8.45 (1H, m), 8.50–9.00 (1H, br s), 12.50 (1H, br s); m/z (M+H)$^+$ 283 (100%).

(g)

247; Yield, 89%; mpt. 228–231° C.; $\delta_H$ 4.25 (2H, s), 6.60–7.05 (3H, m), 7.80–8.00 (3H, m), 8.25–8.45 (1H, m), 9.80 (1H, s), 12.55 (1H, s); m/z (M+H)$^+$ 271 (65%).

(h)

277; Yield, 36%; m.pt. 157–162° C.; $\delta_H$ 3.80 (3H, s), 4.40 (2H, s), 7.3–8.0 (7H, m), 8.2–8.4 (1H, m) and 12.60 (1H, s).

(i)

278; Yield, 6%; m.pt. 131–139° C.; $\delta_H$ 4.40 (2H, s), 7.3–7.9 (12H, m), 8.2–8.4 (1H, m), 10.20 (1H, s) and 12.60 (1H, s); m/z (M+H)$^+$ 356 (79% purity).

(j)

253; $R^{N1}R^{N2}$NH=morpholine

Yield, 19% over 2 stages; m.pt. 118–120° C.; $\delta_H$ 2.3–2.6 (4H, m), 2.7–2.9 (4H, m), 3.4–3.9 (10H, m) 4.35 (2H, s), 7.0–8.3 (11H, m) 9.70 (1H, s) and 12.30 (1H, s); m/z (M+H)$^+$ 540 (95% purity).

254; $R^{N1}R^{N2}$NH=pyrrolidine

Yield, 42% over 2 stages; m.pt. 110–113° C.; $\delta_H$ 1.6–1.8 (4H, m), 2.3–2.6 (4H, m), 2.7–2.9 (4H, m), 3.6–3.9 (6H, m), 4.35 (2H, s), 7.2–8.3 (11H, m) 9.70 (1H, s) and 12.60 (1H, s).

(k)

265;

Yield, 46%; m.pt. decomposes >75° C.; $\delta_H$ 1.9–2.2 (2H, m), 2.7–2.85 (4H, m), 3.5–3.9 (8H, m), 4.20 (2H, s), 7.0 (1H, s), 7.7–8.2 (6H, m), 8.80 (1H, s) and 12.50 (1H, s).

Biological Testing

In order to assess the inhibitory action of the compounds, the following assay was used to determine IC$_{50}$ values.

Mammalian PARP, isolated from Hela cell nuclear extract, was incubated with Z-buffer (25 mM Hepes (Sigma); 12.5 MM MgCl$_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μl.

After 10 minutes incubation at 30° C. the reactions were initiated by the addition of a 10 μl reaction mixture, containing NAD (5 μM), ³H-NAD and 30 mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{(\text{cpm of unknowns} - \text{mean negative cpm})}{(\text{mean positive cpm} - \text{mean negative cpm})}\right)$$

Some results are detailed below in Table 1 as $IC_{50}$ values (the concentration at which 50% of the enzyme activity is inhibited), which are determined over a range of different concentrations, normally from 10 μM down to 0.01 μM. Such $IC_{50}$ values are used as comparative values to identify increased compound potencies.

For comparison, the $IC_{50}$ of 100 (1(2H)-phthalazinone was determined using the above test to be 7.2 μM.

TABLE 1

| Compound | $IC_{50}$ (μM) |
|---|---|
| 126 | 1.8 |
| 129 | 1.6 |
| 132 | 0.7 |
| 141 | 1.4 |
| 151 | 1.8 |
| 186 | 1.1 |
| 191 | 1.3 |
| 211 | 0.4 |
| 248 | 1.0 |
| 139 | 1.7 |
| 163 | 1.8 |
| 192 | 1.4 |
| 138 | 1.2 |
| 142 | 0.7 |
| 193 | 1.0 |
| 194 | 1.4 |
| 164 | 1.8 |
| 165 | 0.3 |
| 276 | 2.5 |
| 277 | 0.6 |
| 159 | 3.5 |
| 160 | 1.3 |
| 166 | 4.1 |
| 167 | 1.6 |
| 227 | 0.4 |
| 169 | 0.6 |
| 170 | 0.4 |
| 171 | 0.6 |
| 172 | 0.09 |
| 215 | 4.0 |
| 216 | 0.3 |
| 206 | 1.2 |
| 179 | 0.04 |
| 212 | 0.9 |
| 213 | 4.4 |
| 239 | 0.6 |
| 180 | 1.3 |

TABLE 1-continued

| Compound | $IC_{50}$ (μM) |
|---|---|
| 222 | 2.2 |
| 247 | 0.5 |
| 241 | 0.9 |
| 198 | 3.8 |
| 204 | 0.7 |
| 202 | 0.07 |
| 131 | 4.4 |
| 177 | 0.8 |
| 178 | 0.2 |
| 249 | 0.7 |
| 145 | 0.8 |
| 90 | 0.9 |
| 91 | 3.3 |
| 92 | 1.3 |
| 93 | 2.1 |

The following compounds were tested and had $IC_{50}$s of less than, or equal to, 1 μM: 233, 278, 279, 294, 295, 601, 604, 624, 640–659, 667–678 and 680–706.

The following compounds were tested and had $IC_{50}$s of less than, or equal to, 3 μM: 253, 254, 265 and 619.

The following compounds were tested and had $IC_{50}$s of less than, or equal to, 5 μM: 266, 283, 284 an 285.

The Dose Enhancing Factor (DEF) is a ratio of the enhancement of cell growth inhibition elicited by the test compound in the presence of bleomycin compared to bleomycin alone. The test compounds were used at a fixed concentration of 25 μM. Bleomycin was used at a concentration of 0.5 μg/ml. The DEF was calculated from the formula:

$$\frac{Growth_{TC}}{Growth_{Control}} \times \frac{Growth_{bleo}}{Growth_{(bleo+TC)}}$$

where $Growth_{TC}$ is cell growth in presence of the test compound;

$Growth_{control}$ is cell growth of control cells;

$Growth_{bleo}$ is cell growth in presence of bleomycin; and $Growth_{(bleo+TC)}$ is cell growth in presence of bleomycin and the test compound.

Cell growth was assessed using the sulforhodamine B (SRB) assay (Skehan, P., et al., 1990, *J. Natl. Cancer Inst.*, 82, 1107–1112). 2,000 HeLa cells were seeded into each well of a flat-bottomed 96-well microtiter plate in a volume of 100 μl and incubated for 6 hours at 37° C. Cells were either replaced with media alone or with media containing the test compound at a final concentration of 25 μM. Cells were allowed to grow for a further 1 hour before the addition of bleomycin to either untreated cells or test compound treated cells. Cells untreated with either bleomycin or test compound were used as a control. Cells treated with test compound alone were used to assess the growth inhibition by the test compound.

Cells were left for a further 16 hours before replacing the media and allowing the cells to grow for a further 72 hours at 37° C. The media was then removed and the cells fixed with 100 μl of ice cold 10% (w/v) trichloroacetic acid. The plates were incubated at 4° C. for 20 minutes and then washed four times with water. Each well of cells was then stained with 100 μl of 0.4% (w/v) SRB in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

Some results are shown in Table 2.

TABLE 2

| Compound | DEF |
|---|---|
| 126 | 1.9 |
| 129 | 1.3 |
| 132 | 2.3 |
| 141 | 1.6 |
| 151 | 1.9 |
| 186 | 1.6 |
| 191 | 1.5 |
| 211 | 1.4 |
| 248 | 1.2 |
| 139 | 1.4 |
| 163 | 1.3 |
| 192 | 1.4 |
| 138 | 1.3 |
| 142 | 1.6 |
| 193 | 2.2 |
| 194 | 1.6 |
| 164 | 1.3 |
| 165 | 1.3 |
| 160 | 1.5 |
| 166 | 1.4 |
| 227 | 2.6 |
| 169 | 1.5 |
| 170 | 2.6 |
| 171 | 1.8 |
| 172 | 1.4 |
| 215 | 1.4 |
| 216 | 1.3 |
| 206 | 1.2 |
| 179 | 1.4 |
| 212 | 2.3 |
| 213 | 1.3 |
| 180 | 1.2 |
| 222 | 1.2 |
| 198 | 2.3 |
| 204 | 1.6 |
| 131 | 1.3 |
| 177 | 1.2 |
| 178 | 1.9 |
| 145 | 1.8 |
| 90 | 1.8 |
| 91 | 1.4 |
| 92 | 1.5 |
| 93 | 1.3 |

The following compounds were tested and had DEFs of greater than 1: 233, 249, 254, 265, 278, 279, 283, 284, 640, 645, 648–654, 655–658, 667, 671, 672, 678, 680, 683, 684 and 686–688.

What is claimed is:

1. A compound of formula:

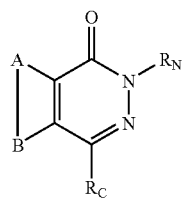

or an isomer, salt, solvate, chemically protected form, and prodrug thereof, wherein:

A and B together represent optionally monosubstituted, fused benzene;

$R_C$ is —$CH_2$—$R_L$;

$R_L$ is substituted phenyl, wherein the substituents are selected from the group consisting of:

$C_{3-20}$ heterocyclyl; ester; amido; acyloxy; sulfonamido; ureido; and optionally further substituted; and $R_N$ is hydrogen.

2. A compound according to claim 1, wherein the fused benzene is unsubstituted.

3. A compound according to claim 1, wherein $R_L$ is substituted by a ureido group, or a sulfonamido group.

4. A pharmaceutical composition comprising a compound of formula:

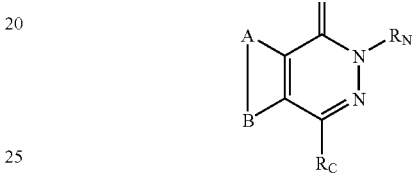

or an isomer, salt, solvate, chemically protected form, and prodrug thereof, wherein:

A and B together represent an optionally substituted, fused benzene;

$R_C$ is —$CH_2$—$R_L$;

$R_L$ is optionally substituted phenyl; and $R_N$ is hydrogen;

and a pharmaceutically acceptable carrier or diluent.

5. The pharmaceutical composition of claim 4, wherein the fused benzene is unsubstituted.

6. The pharmaceutical composition of claim 4, wherein $R_L$ is substituted by one or more substituents selected from the group consisting of: $C_{1-7}$ alkyl; $C_{5-20}$ aryl; $C_{3-20}$ heterocyclyl; halo; hydroxy; ether; nitro; cyano; carbonyl groups; amino; sulfonamido; ureido; acyloxy; thiol; thioether; sulfoxide; and sulfone.

7. The pharmaceutical composition of claim 6, wherein $R_L$ is substituted by a ureido group, or a sulfonamido group.

8. A compound of the formula:

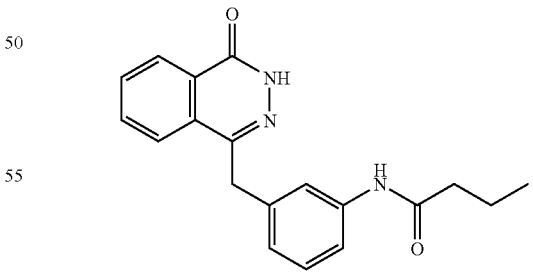

or an isomer, salt, solvate, chemically protected form and prodrug thereof.

* * * * *